United States Patent
Mourad et al.

(10) Patent No.: US 7,022,077 B2
(45) Date of Patent: Apr. 4, 2006

(54) SYSTEMS AND METHODS FOR MAKING NONINVASIVE ASSESSMENTS OF CARDIAC TISSUE AND PARAMETERS

(75) Inventors: Pierre D. Mourad, Seattle, WA (US); Michel Kliot, Bellevue, WA (US); Rex Patterson, Kirkland, WA (US); Alec Rooke, Shoreline, WA (US)

(73) Assignees: Allez Physionix Ltd., Seattle, WA (US); University of Washington, Seattle, WA (US)

( * ) Notice: Subject to any disclaimer, the term of this patent is extended or adjusted under 35 U.S.C. 154(b) by 97 days.

(21) Appl. No.: 10/612,483

(22) Filed: Jul. 1, 2003

(65) Prior Publication Data

US 2004/0059220 A1 Mar. 25, 2004

Related U.S. Application Data

(63) Continuation-in-part of application No. 09/995,897, filed on Nov. 28, 2001, now Pat. No. 6,875,176.

(60) Provisional application No. 60/475,803, filed on Jun. 3, 2003, provisional application No. 60/393,293, filed on Jul. 1, 2002, provisional application No. 60/253,959, filed on Nov. 28, 2000.

(51) Int. Cl.
*A61B 8/14* (2006.01)

(52) U.S. Cl. ..................... 600/449; 600/453
(58) Field of Classification Search ........ 600/407–472, 600/481, 510; 128/916; 73/595, 602
See application file for complete search history.

(56) References Cited

U.S. PATENT DOCUMENTS 5,086,775 A 2/1992 Parker et al.
5,474,070 A 12/1995 Ophir et al.
5,524,636 A 6/1996 Sarvazyan et al.
5,533,510 A 7/1996 Koch, III et al.
5,606,971 A 3/1997 Sarvazyan
5,678,565 A 10/1997 Sarvazyan
5,810,731 A 9/1998 Sarvazyan et al.
5,830,131 A 11/1998 Caro et al.
5,903,516 A 5/1999 Greenleaf et al.
5,921,928 A 7/1999 Greenleaf et al.
6,039,691 A 3/2000 Walker et al.
6,099,471 A 8/2000 Torp et al.
6,328,694 B1 12/2001 Michaeli
6,517,485 B1 2/2003 Torp et al.
6,527,717 B1 3/2003 Jackson et al.
6,537,221 B1 3/2003 Criton et al.

(Continued)

OTHER PUBLICATIONS

Sugimoto, Tsuneyoshi et al., "Tissue Hardness Measurement Using the Radiation Force of Focused Ultrasound", *Ultrasonics Symposium*, pp. 1377-1380 (1990).

(Continued)

*Primary Examiner*—Ali Imam
(74) *Attorney, Agent, or Firm*—Speckman Law Group PLLC; Ann W. Speckman

(57) ABSTRACT

Systems and methods for noninvasive assessment of cardiac tissue properties and cardiac parameters using ultrasound techniques are disclosed. Determinations of myocardial tissue stiffness, tension, strain, strain rate, and the like, may be used to assess myocardial contractility, myocardial ischemia and infarction, ventricular filling and atrial pressures, and diastolic functions. Non-invasive systems in which acoustic techniques, such as ultrasound, are employed to acquire data relating to intrinsic tissue displacements are disclosed. Non-invasive systems in which ultrasound techniques are used to acoustically stimulate or palpate target cardiac tissue, or induce a response at a cardiac tissue site that relates to cardiac tissue properties and/or cardiac parameters are also disclosed.

20 Claims, 10 Drawing Sheets

U.S. PATENT DOCUMENTS 6,579,240 B1    6/2003   Bjaerum et al.

OTHER PUBLICATIONS

Hoffman, et al. "Strain Rate Measurement by Doppler Echocardiography Allows Improved Assessment of Myocardial Viability in Patients With Depressed Left Ventricular Function," *Journal of the American College of Cardiology*, 2002, vol. 39, No. 3, pp. 443-449.

Pislaru, et al. "Higher Myocardial Strain Rates During Isovolumic Relaxation Phase Than During Ejection Characterize Acutely Ischemic Myocardium," *Journal of the American College of Cardiology*, 2002, vol. 40, No. 8, pp. 1487-1494.

Vogel, et al. "Noninvasive Assessment of Left Ventricular Force-Frequency Relationships Using Tissue Doppler-Derived Isovolumic Acceleration: Validation in an Animal Model," *Circulation*, 2003, vol. 107, pp. 1647-1652.

Weidemann, et al, "Defining the Transmurality of a Chronic Myocardial Infarction by Ultrasonic Strain-Rate Imaging: Implications for Identifying Intramural Viability: An Experimental Study," *Circulation*, 2003, vol. 107, pp. 883-888.

SYSTEMS AND METHODS FOR MAKING NONINVASIVE ASSESSMENTS OF CARDIAC TISSUE AND PARAMETERS

REFERENCE TO PRIORITY APPLICATION

This application claims priority to U.S. Provisional Application No. 60/393,293 filed Jul. 1, 2002 and U.S. Provisional Application No. 60/475,803 filed Jun. 3, 2003. This application is also a continuation-in-part of U.S. patent application Ser. No. 09/995,897, filed Nov. 28, 2001, issued as U.S. Pat. No. 6,875,176 on Apr. 4, 2005, which claims priority to U.S. Provisional Application No. 60/253,959, filed Nov. 28, 2000.

TECHNICAL FIELD OF THE INVENTION

This invention relates to systems and methods for assessing cardiac tissue and cardiac parameters noninvasively using ultrasound techniques.

BACKGROUND OF THE INVENTION

Methods and systems for determining and characterizing various systems and tissue properties are known. Characterization of internal tissues using non-invasive and non-traumatic techniques is challenging in many areas. Non-invasive detection of various cancers remains problematic and unreliable. Similarly, non-invasive assessment and monitoring of important internal clinical parameters, such as intracranial pressure and cardiac output, are also practical challenges, despite the efforts devoted to developing such techniques.

Ultrasound imaging is a non-invasive, diagnostic modality that is capable of providing information relating to tissue properties. In the field of medical imaging, ultrasound may be used in various modes to produce images of objects or structures within a patient. In a transmission mode, an ultrasound transmitter is placed on one side of an object and the sound is transmitted through the object to an ultrasound receiver. An image may be produced in which the brightness of each image pixel is a function of the amplitude of the ultrasound that reaches the receiver (attenuation mode), or the brightness of each pixel may be a function of the time required for the sound to reach the receiver (time-of-flight mode). Alternatively, if the receiver is positioned on the same side of the object as the transmitter, an image may be produced in which the pixel brightness is a function of the amplitude of reflected ultrasound (reflection or backscatter or echo mode). In a Doppler mode of operation, the tissue (or object) is imaged by measuring the phase shift of the ultrasound reflected from the tissue (or object) back to the receiver.

Ultrasonic transducers for medical applications are constructed from one or more piezoelectric elements activated by electrodes. Such piezoelectric elements may be constructed, for example, from lead zirconate titanate (PZT), polyvinylidene diflouride (PVDF), PZT ceramic/polymer composites, and the like. The electrodes are connected to a voltage source, a voltage waveform is applied, and the piezoelectric elements change in size at a frequency corresponding to that of the applied voltage. When a voltage waveform is applied, the piezoelectric elements emit an ultrasonic wave into the media to which it is coupled at the frequencies contained in the excitation waveform. Conversely, when an ultrasonic wave strikes the piezoelectric element, the element produces a corresponding voltage across its electrodes. Numerous ultrasonic transducer constructions are known in the art.

When used for imaging, ultrasonic transducers are provided with several piezoelectric elements arranged in an array and driven by different voltages. By controlling the phase and amplitude of the applied voltages, ultrasonic waves combine to produce a net ultrasonic wave that travels along a desired beam direction and is focused at a selected point along the beam. By controlling the phase and the amplitude of the applied voltages, the focal point of the beam can be moved in a plane to scan the subject. Many such ultrasonic imaging systems are well known in the art.

An acoustic radiation force is exerted by an acoustic wave on an object in its path. The use of acoustic radiation forces produced by an ultrasound transducer has been proposed in connection with tissue hardness measurements. See Sugimoto et al., "Tissue Hardness Measure Using the Radiation Force of Focused Ultrasound", IEEE Ultrasonics Symposium, pp. 1377–80, 1990. This publication describes an experiment in which a pulse of focused ultrasonic radiation is applied to deform the object at the focal point of the transducer. The deformation is measured using a separate pulse-echo ultrasonic system. Measurements of tissue hardness are made based on the amount or rate of object deformation as the acoustic force is continuously applied, or by the rate of relaxation of the deformation after the force is removed.

Another system is disclosed by T. Sato, et al., "Imaging of Acoustical Nonlinear Parameters and Its Medical and Industrial Applications: A Viewpoint as Generalized Percussion," Acoustical Imaging, Vo. 20, pg. 9–18, Plenum Press, 1993. In this system, a lower frequency wave (350 kHz) is used as a percussion force, and an ultrasonic wave (5 MHz) is used in a pulse-echo mode to produce an image of the subject. The percussion force perturbs second order nonlinear interactions in tissues, which may reveal more structural information than conventional ultrasound pulse-echo systems.

Fatemi and Greenleaf reported an imaging technique that uses acoustic emission to map the mechanical response of an object to local cyclic radiation forces produced by interfering ultrasound beams. The object is probed by arranging the intersection of two focused, continuous-wave ultrasound beams of different frequencies at a selected point on the object. Interference in the intersection region of the two beams produces modulation of the ultrasound energy density, which creates a vibration in the object at the selected region. The vibration produces an acoustic field that can be measured. The authors speculate that ultrasound-stimulated vibro-acoustic spectrography has potential applications in the non-destructive evaluation of materials, and for medical imaging and noninvasive detection of hard tissue inclusions, such as the imaging of arteries with calcification, detection of breast microcalcifications, visualization of hard tumors, and detection of foreign objects.

U.S. Pat. Nos. 5,903,516 and 5,921,928 (Greenleaf et al.) disclose a method and system for producing an acoustic radiation force at a target location by directing multiple high frequency sound beams to intersect at the desired location. A variable amplitude radiation force may be produced using variable, high frequency sound beams, or by amplitude modulating a high frequency sound beam at a lower, baseband frequency. The mechanical properties of an object, or the presence of an object, may be detected by analyzing the acoustic wave that is generated from the object by the applied acoustic radiation force. An image of the object may be produced by scanning the object with high frequency sound beams and analyzing the acoustic waves generated at each scanned location. The mechanical characteristics of an object may also be assessed by detecting the motion produced at the intersections of high frequency sound beams and analyzing the motion using Doppler ultrasound and nuclear magnetic resonance imaging techniques. Variations in the characteristics of fluids (e.g. blood), such as fluid temperature, density and chemical composition can also be detected by assessing changes in the amplitude of the beat frequency signal. Various applications are cited, including detection of atherosclerosis, detection of gas bubbles in fluids, measurement of contrast agent concentration in the blood stream, object position measurement, object motion and velocity measurement, and the like. An imaging system is also disclosed.

U.S. Pat. No. 6,039,691 (Walker et al.) discloses methods and apparatus for soft tissue examination employing an ultrasonic transducer for generating an ultrasound pulse that induces physical displacement of viscous or gelatinous biological fluids and analysis techniques that determine the magnitude of the displacement. The transducer receives ultrasonic echo pulses and generates data signals indicative of the tissue displacement. This apparatus and method is particularly useful for examining the properties of a subject's vitreous body, in connection with the evaluation and/or diagnosis of ocular disorders, such as vitreous traction.

U.S. Pat. No. 5,086,775 (Parker et al.) describes a system in which a low frequency vibration source is used to generate oscillations in an object, and a coherent or pulsed ultrasound imaging system is used to detect the spatial distribution of the vibration amplitude or speed of the object in real-time. In particular, the reflected Doppler shifted waveform generated is used to compute the vibration amplitude and frequency of the object on a frequency domain estimator basis, or on a time domain estimator basis. Applications of this system include examination of passive structures such as aircraft, ships, bridge trusses, as well as soft tissue imaging, such as breast imaging.

Several U.S. patents to Sarvazyan relate to methods and devices for ultrasonic elasticity imaging for noninvasively identifying tissue elasticity. Tissue having different elasticity properties may be identified, for example, by simultaneously measuring strain and stress patterns in the tissue using an ultrasonic imaging system in combination with a pressure sensing array. The ultrasonic scanner probe with an attached pressure sensing array may exert pressure to deform the tissue and create stress and strain in the tissue. This system may be used, for example, to measure mechanical parameters of the prostate. U.S. patents to Sarvazyan also describe shear wave elasticity imaging using a focused ultrasound transducer that remotely induces a propagating shear wave in tissue. Shear modulus and dynamic shear viscosity at a given site may be determined from the measured values of velocity and attenuation of propagating shear waves at that site.

Cardiac Performance

Cardiac output is important to the body for two reasons. The major limitation in the delivery of nutrients to the tissues of the body is the delivery of oxygen. Delivery of metabolic substrates ("food") and elimination of waste products require less blood flow than is necessary for adequate delivery of oxygen for the tissues' metabolic needs. An inadequate cardiac output translates into some tissues of the body receiving too little oxygen and leads to dysfunction of the affected organ or even tissue damage or cell death of the deprived tissue.

The "gold standard" for measurement of cardiac output is the pulmonary artery catheter. It measures cardiac output via the thermodilution technique. It is effective, and not difficult to use, but it requires placing the catheter into a vein and threading the catheter through the heart and into the lungs. The risks to the patient from using the pulmonary artery catheter preclude routine use. Echocardiography can be used, either transthoracically or using esophageal echo. This technique is safer to the patient, but it is technically more difficult, less accurate, and impractical to use for longer than a few minutes at a time. Other techniques exist, but none have gained universal acceptance. A low risk method for measuring either cardiac output, or providing a good estimation of the components of cardiac output, would prove invaluable in critical care settings. Such a technique would likely be used in far more patients than is the number of patients who currently receive a pulmonary artery catheter.

Cardiac output is the product of heart rate and stroke volume (the amount of blood the heart pumps to the body in a single beat). Heart rate is easy to determine. Stroke volume is difficult to measure directly, so it is generally calculated by measuring or estimating cardiac output and then deriving stroke volume=cardiac output÷heart rate. The objective of providing a non-invasive measurement of cardiac output thus becomes a problem of how to measure stroke volume in a non-invasive fashion. Heart rate is also usually easy to manipulate. Consequently, the difficult aspect in the clinical manipulation of cardiac output is generally reduced to a problem of how to manipulate stroke volume.

Stroke volume is a function of two basic properties of the heart: volume status and contractility. Each of these parameters is as important to blood pressure as vascular resistance and heart rate. Although the volume status of a patient is manipulated by increasing or decreasing the blood volume of the body, what is really important is the volume status of the right and left ventricles. The ventricles need to be "filled up" prior to contraction for two reasons. First, the ventricles cannot pump to the lungs or body (right and left ventricles, respectively) what the ventricles don't have in them at the start of contraction. The more blood in the chamber of the ventricle, the more blood could be potentially pumped out. Second, as more blood is put in the ventricle, the muscle cells of the heart become more stretched. The greater the stretch, the harder the heart muscle contracts at the next heartbeat. This phenomenon is known as the length-tension relationship, and is illustrated in FIG. 1. Stronger contractions permit the heart to pump against a higher blood pressure and/or pump out a higher percentage of the blood in the ventricle. Expressed mathematically, stroke volume (SV) is equal to the product of end-diastolic volume (EDV, the amount of blood in the chamber of the ventricle just before contraction begins) and the ejection fraction (EF, the percent of the EDV that is pushed out of the ventricle during heart contraction). SV=EDV x EF.

When treating a patient who is thought to have a low stroke volume, a common clinical maneuver is to administer fluid. In a normal heart, the EF will not decrease even if blood pressure increases as a result of the improved stroke volume. However, a heart with poorly functioning muscle will have a low EF at baseline and will not demonstrate much of an improvement in its contraction when EDV is increased (See FIG. 1). In fact, more volume may worsen the status of the patient if the heart does not improve its performance in response to the volume. If performance does not improve, the heart may become distended, which results in impaired function. Furthermore, even if over-distention does not occur, the increase in volume increases the filling pressures, that in turn must be matched by increased pressures in the atrium and veins. In the case of the right ventricle, high venous pressures cause congestion in the abdominal organs and legs that can lead to liver and intestinal dysfunction and to peripheral edema. In the case of the left ventricle, high venous pressures cause the pressure in the blood vessels in the lungs to increase. If these pressures get too high, fluid leaks out into the lungs and causes symptoms of heart failure (shortness of breath, inability to lay flat) or even pulmonary edema, a life-threatening event where the air sacs in the lung fill with fluid and limit the ability to get oxygen into the blood.

It is therefore important to know when giving a patient more fluid would produce these undesirable side effects. Current technology for this determination largely rests with the application of the pulmonary artery catheter. The catheter can measure the pressure in the atria and thus provide an estimate of the pressure in the ventricular chamber during diastole when the heart muscle is relaxed. If these pressures are already high, then more fluid must be administered with great care, if at all. Unfortunately, interpretation of pressures provided by the pulmonary artery catheter can be difficult, making optimal fluid management problematic. The difficulty, in part, is that the relationship between the filling pressure (end-diastolic pressure) and volume (end-diastolic volume) is not linear. FIG. 2 illustrates this relationship between end-diastolic pressure and volume for heart tissue that is stiff and compliant. A change in pressure of a few mmHg could represent a big or a small change in ventricular volume, depending on the character of the heart tissue. Furthermore, as the condition of the heart changes, the curve can shift around making it harder to interpret the pressure measurements as a measure of end-diastolic volume.

Ideally, clinicians would like to have a direct measure of end-diastolic volume. An echocardiogram may provide a volume measurement, but this measurement does not tell the clinician whether that volume is too high, too low or just right. Measurement of ventricular wall stiffness, if it could be provided, would be helpful because wall stiffness is directly affected by ventricular pressure. In fact, knowledge of a wall stiffness parameter may be more useful than knowledge of a pressure parameter because stiffness is also affected by ventricular size. Measurement of a ventricular wall stiffness parameter is likely to be more effective than measurement of a pressure parameter in determining when fluid volume administration will be ineffective or even harmful to a patient.

Ultrasound techniques, such as Doppler tissue imaging modes, have recently been proposed for use in the diagnosis of cardiac tissue and function. In general, these techniques involve tracking of tissue movement, or velocity. Tissue velocities are used to derive an estimate of strain rate, and from strain rate, an estimation of tissue strain may be derived. These techniques are dependent on accurate tissue motion estimates, when tissues are moving in different directions within a small spatial region.

U.S. Pat. No. 6,527,717 discloses systems and methods for analyzing tissue motion in which motion estimates are corrected for transducer motion. Tissue motion may be used to determine a strain rate or strain, and motion estimates may be generated using data acquired by an intracardiac transducer array.

U.S. Pat. No. 6,099,471 discloses ultrasound techniques for determining strain velocity from tissue velocity. Tissue velocity is determined based on measurements of the pulse-to-pulse Doppler shift at positions along an ultrasound beam.

U.S. Pat. No. 6,517,485 discloses ultrasound systems and methods for calculating and displaying tissue deformation parameters, such as tissue Doppler and strain rate imaging. U.S. Pat. No. 6,537,221 relates to strain rate analysis for ultrasound images in which the spatial gradient of velocity is calculated in the direction of tissue motion. U.S. Pat. No. 6,579,240, discloses ultrasound display of a moving structure, such as a cardiac wall tissue within a region of interest, as a color representation.

The accuracy and clinical usefulness of tissue strain predictions based on the estimation of strain rate from Doppler tissue velocities is problematic. Existing methods of measuring ventricular filling and cardiac contractility using intra-arterial lines or echocardiograms have limited application because of the risk to the patient, high expense and difficulty in interpretation of the information provided. Lack of direct, non-invasive and inexpensive methods to measure ventricular filling and cardiac contractility means that optimal management of stroke volume is missing from the care of many patients who would benefit from such optimization.

Arterial Blood Pressure

Arterial blood pressure (ABP) is a fundamental objective measure of the state of an individual's health. Indeed, it is considered a "vital sign" and is of critical importance in all areas of medicine and healthcare. The accurate measure of ABP assists in determination of the state of cardiovascular and hemodynamic health in stable, urgent, emergent, and operative conditions, indicating appropriate interventions to maximize the health of the patient.

Currently, ABP is most commonly measured noninvasively using a pneumatic cuff, often described as pneumatic plethysmography or Korotkoff's method. While this mode of measurement is simple and inexpensive to perform, it does not provide the most accurate measure of ABP, and it is susceptible to artifacts resulting from the condition of arterial wall, the size of the patient, the hemodynamic status of the patient, and autonomic tone of the vascular smooth muscle. Additionally, repeated cuff measurements of ABP result in falsely elevated readings of ABP, due to vasoconstriction of the arterial wall. To overcome these problems, and to provide a continuous measure of ABP, invasive arterial catheters are used. While such catheters are very reliable and provide the most accurate measure of ABP, they require placement by trained medical personnel, usually physicians, and they require bulky, sophisticated, fragile, sterile instrumentation. Additionally, there is a risk of permanent arterial injury causing ischemic events when these catheters are placed. As a result, these invasive monitors are only used in hospital settings and for patients who are critically ill or are undergoing operative procedures.

U.S. Pat. No. 4,869,261 to Penaz discloses a method for automatic, non-invasive determination of continuous arterial blood pressure in arteries compressible from the surface by first determining a set point with a pressure cuff equipped with a plethysmographic gauge of vascular volume and then maintaining the volume of the measured artery constant to infer arterial blood pressure. A generator producing pressure vibrations superimposed on the basic blood pressure wave, and the changes in the oscillations of the blood pressure wave are monitored by an active servo-system that constantly adjusts the cuff pressure to maintain constant arterial volume; thus, the frequency of vibration of the blood pressure wave that is higher than the highest harmonic component of the blood pressure wave is used to determine arterial blood pressure.

U.S. Pat. No. 4,510,940 to Wesseling discloses a method for correcting the cuff pressure in the indirect, non-invasive and continuous measurement of the blood pressure in a part of the body by first determining a set-point using a plethysmograph in a fluid-filled pressure cuff wrapped around an extremity and then adjusting a servo-reference level as a function of the shape of the plethysmographic signal, influenced by the magnitude of the deviation of the cuff pressure adjusted in both open and closed systems.

U.S. Pat. No. 5,241,964 to McQuilkin discloses a method for a non-invasive, non-occlusive method and apparatus for continuous determination of arterial blood pressure using one or more Doppler sensors positioned over a major artery to determine the time-varying arterial resonant frequency and hence blood pressure. Alternative methods including the concurrent use of proximal and distal sensors, impedance plethysmography techniques, infrared percussion sensors, continuous oscillations in a partially or fully inflated cuff, pressure transducers or strain gauge devices applied to the arterial wall, ultrasonic imaging techniques which provide the time-varying arterial diameter or other arterial geometry which changes proportionately with intramural pressure, radio frequency sensors, or magnetic field sensors are also described.

U.S. Pat. No. 5,830,131 to Caro et al. discloses a method for determining physical conditions of the human arterial system by inducing a well-defined perturbation (exciter waveform) of the blood vessel in question and measuring a hemo-parameter containing a component of the exciter waveform at a separate site. The exciter consists of an inflatable bag that can exert pressure on the blood vessel of interest, and is controlled by a processor. Physical properties such as cardiovascular disease, arterial elasticity, arterial thickness, arterial wall compliance, and physiological parameters such as blood pressure, vascular wall compliance, ventricular contractions, vascular resistance, fluid volume, cardiac output, myocardial contractility, etc. are described.

U.S. Pat. No. 4,646,754 to Seale discloses a method for non-invasively inducing vibrations in a selected element of the human body, including blood vessels, pulmonary vessels, and eye globe, and detecting the nature of the responses for determining mechanical characteristics of the element. Methods for inducing vibrations include mechanical drivers, while methods for measuring responses include ultrasound, optical means, and visual changes. Mechanical characteristics include arterial blood pressure, organ impedance, intraocular pressure, and pulmonary blood pressure.

U.S. Pat. No. 5,485,848 to Jackson et al. discloses a method and apparatus for non-invasive, continuous arterial blood pressure determination using a separable, diagnostically accurate blood pressure measuring device, such as a conventional pressure cuff, to initially calibrate the system and then measuring arterial wall movement caused by blood flow through the artery to determine arterial blood pressure. Piezoelectric devices are used in wristband device to convert wall motion signals to an electric form that can be analyzed to yield blood pressure.

U.S. Pat. No. 5,749,364 to Sliwa, Jr. et al. discloses a method and apparatus for the determination of pressure and tissue properties by utilizing changes in acoustic behavior of micro-bubbles in a body fluid, such as blood, to present pressure information. This invention is directed at the method of mapping and presenting body fluid pressure information in at least two dimensions and to an enhanced method of detecting tumors.

PCT International Patent Publication WO 00/72750 to Yang et al. discloses a method and apparatus for the non-invasive, continuous monitoring of arterial blood pressure using a finger plethysmograph and an electrical impedance photoplethysmograph to monitor dynamic behavior of arterial blood flow. Measured signals from these sensors on an arterial segment are integrated to estimate the blood pressure in this segment based on a hemodynamic model that takes into account simplified upstream and downstream arterial flows within this vessel.

A noninvasive, continuous ABP monitor would provide medical personnel with valuable information on the hemodynamic and cardiovascular status of the patient in any setting, including the battlefield, emergency transport, clinic office, and triage clinics. Additionally, it would provide clinicians the ability to continuously monitor the ABP of a patient in situations where the risks of an invasive catheter are unwarranted or unacceptable (e.g., outpatient procedures, ambulance transports, etc.). Thus, the present invention is directed to methods and systems for the continuous assessment of ABP using non-invasive ultrasound techniques.

SUMMARY OF THE INVENTION

The present invention provides methods and systems using the application of ultrasound for noninvasively assessing, localizing and monitoring cardiac properties and parameters, and for diagnosing, localizing and monitoring various conditions, responses and disease states. Acoustic properties of tissues, including cardiac tissues, and tissue displacement, may be evaluated using the methods and systems described herein, as well as the techniques described in PCT International Publication WO 02/43564, which is incorporated herein by reference in its entirety.

Acoustic properties of cardiac tissue may be determined, for example, by collecting acoustic scatter data using an ultrasound transducer, or transducer array, aimed at, or having a focus on or in cardiac tissue. In a "passive" mode embodiment, measurements of the "intrinsic" properties of cardiac tissue, in situ, such as tissue stiffness or tension or strain, etc., are taken using ultrasound techniques. In another embodiment, focused ultrasound beam(s) are applied to cardiac tissue to deform localized cardiac tissue, and one or more aspect(s) of the deformation, or a biological response produced by the deformation(s), is assessed and related to cardiac tissue properties and parameters. The (intrinsic or induced) acoustic properties of cardiac tissue, such as (intrinsic or induced) displacements of target tissue sites, are related to physical and/or structural tissue properties, such as tissue stiffness, distension, tension, strain, strain rate, elasticity, compliance and the like, which are related to clinically important cardiac parameters and properties, such as cardiac output.

In another embodiment, an oscillatory radiation force is applied to localized cardiac tissue to induce localized tissue oscillations. Acoustic emissions produced by the oscillating cardiac tissue, and/or other properties of the oscillating tissue, are related to the properties of the cardiac tissue and may be related, according to the present invention, to specified cardiac parameters and properties. In yet another embodiment, focused ultrasound beam(s) are used to make local sonoelasticity measurements to assess the properties of cardiac tissue. For some applications, observations of changes and trends in the properties of targeted cardiac tissue over time are desired, rather than absolute measurements of targeted cardiac tissue properties at a given time.

The methods and systems of the present invention provide important information about the health and condition of cardiac tissue, such as ventricular wall stiffness. By the law of LaPlace, wall stiffness is a function of ventricular chamber volume, ventricular wall thickness and the pressure in the ventricular chamber. If the heart muscle is contracting, then wall stiffness increases, if for no other reason than the ventricular chamber pressure increases. From these first principles a wide variety of useful information can be extracted from the measurement of myocardial tissue properties, such as wall stiffness, at various times throughout the cardiac cycle.

The cardiac cycle is divided into systole and diastole. During systole the heart muscle contracts and blood is ejected. During diastole the muscle relaxes and the ventricular chamber fills with blood from the atrium. FIG. 3 illustrates the pressure and volume relationships of blood in the left and right ventricles during cardiac cycling. The volume of blood in the ventricle just before ejection begins is called the end-diastolic volume (Point A, FIG. 3) and is associated with the end-diastolic pressure (Point B, FIG. 3). Ventricular end-diastolic volume affects both wall thickness (the wall thins as the heart fills) and end-diastolic pressure (pressure goes up as volume increases, but in a non-linear fashion). At end-diastole, the ventricular muscle should be maximally relaxed, and wall stiffness is therefore determined by the intrinsic stiffness of the muscle, ventricular chamber volume, wall thickness and end-diastolic pressure. Consequently, ventricular wall stiffness at the end of diastole is heavily influenced by end-diastolic volume. Ventricular wall stiffness is thus a good parameter, measurable using methods and systems of the present invention, for determining end-diastolic volume and pressure.

Determinations of cardiac wall stiffness parameters provide useful information throughout the cardiac cycle, and not just at end-diastole. Examination of the pressure and volume relationships during the cardiac cycle, as shown in FIG. 3, reveals that ventricular chamber pressure changes continually (in this example, the left ventricle). Of particular interest are the periods when the ventricle begins to fill (Point C, when the atrial pressure exceeds the ventricular pressure); when the ventricle is rapidly relaxing (Period D); and when the ventricle is rapidly developing pressure (Period E). The changes in wall stiffness during Period D, along with the wall stiffness at Point B, are useful in the assessment of ventricular relaxation and in the diagnosis of diastolic dysfunction. The changes in wall stiffness during Period E are useful in the assessment of ventricular contraction (contractility) and the diagnosis of systolic dysfunction.

It is important to understand that at the end of ventricular contraction, the ventricle has squeezed down on itself and is similar to a compressed spring ready to recoil open. "Springing" open is exactly what the ventricle will do if the muscular contraction relaxes quickly enough. If allowed to spring open, the ventricle will literally suck blood into it from the atrium. This phenomenon results in a rapid transfer of blood into the ventricle, more so than for the rest of diastole. FIG. 4A illustrates the flow of blood into a normal ventricle. The E wave is the initial rapid filling as the ventricle draws in blood. Thereafter there is modest filling during the middle of diastole followed by another increase in filling when the atrium contracts (A wave) and forces more blood into the ventricle. FIG. 4B shows the pattern of filling in an abnormal circumstance. When the ventricular muscle does not relax rapidly (diastolic dysfunction), the residual muscle activity present at the beginning of filling does not permit the ventricle to spring open and limits the amount of blood entering the ventricle in early diastole. The rest of the diastolic period must now make up for that limited filling in early diastole—in this circumstance, the A wave is larger than the E wave. To accomplish this make-up filling, the atrium must increase in pressure, and this pressure increase is transmitted to both the ventricle and the organs upstream of the atrium (such as the lungs). If the pressure gets too high, then heart failure symptoms appear, such as pulmonary congestion.

At one time, heart failure was thought to be due exclusively to poor contractility. Now it is understood that diastolic dysfunction alone can cause heart failure. The problem is that diastolic dysfunction cannot be diagnosed as easily as just described. For example, old age causes the abnormal filling pattern shown in FIG. 4B to develop. Furthermore, as atrial pressure increases, the E wave becomes bigger, thereby preventing the appearance of a diminished E wave to diagnose diastolic dysfunction.

The clinical diagnosis of diastolic dysfunction is relatively easy if a pulmonary artery catheter is placed. If the patient has normal left ventricular function, yet the pulmonary artery catheter reveals a high left atrial pressure, then the diagnosis is confirmed. However, most clinicians are unwilling to place a pulmonary artery catheter, so a great deal of effort has been made to estimate left atrial pressure using echocardiography. At present, all the techniques that have been proposed have met with very limited success. Certainly there is no consensus on how to diagnose diastolic dysfunction with echocardiography alone. The ability to make determinations of cardiac properties and parameters noninvasively, such as cardiac tissue stiffness and contractility, however, makes the diagnosis of diastolic dysfunction trivially easy (and non-invasive) because wall stiffness in late diastole reflects left atrial pressure.

Even more information may be obtained by examining wall stiffness during late systole. The intrinsic defect in diastolic dysfunction is abnormally slow relaxation of the ventricular muscle at the end of the contraction. The portion of the cardiac cycle between the end of ejection and the opening of the mitral valve is known as isovolumic relaxation. During this time, wall stiffness is directly proportional to the magnitude of the muscular contraction. This is because the ventricular chamber pressure is being generated by the muscle activity, and the chamber size is not changing, as the ventricle is neither emptying nor filling. Therefore the rate at which wall stiffness decreases directly reflects the rate at which the muscle relaxes. The presence of slow relaxation would therefore provide direct evidence of diastolic dysfunction. Examination of wall stiffness during isovolumic relaxation and at the end of diastole should revolutionize the diagnosis of diastolic dysfunction because the procedure is simple, non-invasive and provides unambiguous results.

The methods and systems of the present invention provide high time resolution information on myocardial tension (strain) throughout the cardiac cycle. Strain measurements can be further manipulated to yield strain rate, the rate of change in strain over time. This approach is fundamentally different from the technologies that use measurement of myocardial tissue velocities to predict strain rate and strain. The present invention provides a direct determination of tissue strain, so that strain no longer has to be referenced to an arbitrary zero as a consequence of the use of integration to determine strain from strain rate. Specifically, methods and systems of the present invention provide determinations of myocardial contractility, myocardial strain and strain rate; detection of myocardial ischemia and infarction; determination of ventricular filling; and detection of diastolic dysfunction. Each of these particular applications is discussed below.

Myocardial Contractility

Classically, myocardial contractility has been defined as either dP/dt, the rate of change of intraventricular pressure, or as peak elastance as determined by the highest value of the intraventricular pressure—ventricular volume ratio during systole. dP/dt peaks during isovolumic contraction and therefore is relatively, but not completely, uninfluenced by loading conditions. The major drawback is that measurement of intraventricular pressure requires the invasive placement of a catheter into the ventricular chamber. Peak elastance not only requires ventricular pressure measurements, but ventricular volume measurements as well. Less accurate, but clinically useful estimates of peak elastance have been achieved with non-invasive brachial blood pressure measurements and echocardiographic estimates of ventricular volume or area.

Several methods have been applied in the laboratory in attempts to quantify contractility. One method involves placing a catheter in the chamber of the left ventricle and measuring how rapidly pressure develops during ventricular contraction. FIG. 5 shows a sample intraventricular pressure tracing (bottom panel) and the rate of change in pressure tracing (dP/dT, top panel). The slope of the intraventricular trace equals the rate of change in pressure at any given instant. Usually, contractility is considered proportional to the maximum rate of change in pressure observed during the contraction (peak value of the dP/dT trace). Ventricles with high contractility contract more rapidly and exhibit a higher value for dP/dT. The peak rate of pressure development occurs before the ventricle begins to eject blood. This means that the volume of the ventricle is not changing and that wall tension is strictly proportional to the ventricular chamber pressure. Wall stiffness directly reflects both wall tension and chamber pressure. Contractility can therefore be estimated as the maximum rate of change in wall stiffness during the onset of contraction.

Peak systolic strain rate correlates with peak dP/dt and with peak elastance. See, e.g., Pislaru C, Abraham T P, Belohlavek M: Strain and strain rate echocardiography. Curr Opin Cardiol 2002; 17:443–454; and Weidemann F, Jamal F, Sutherland G R et al.: Myocardial function defined by strain rate and strain during alterations in inotropic states and heart rate, Am J Physiol Heart Circ Physiol 2002;283: H792–H799. The maximum rate of tissue acceleration (rate of velocity increase) also correlates with dP/dt and elastance when the heart is subjected to positive or negative inotropic agents. See, e.g., Vogel M, Cheung MMH, Li J et al.: Noninvasive assessment of left ventricular force-frequency relationships using tissue doppler-derived isovolumic acceleration, Circulation 2003; 107:1647–1652.

Peak strain rate may thus provide the best clinical estimation of myocardial contractility, particularly if strain rates can be measured in a completely non-invasive fashion. Currently, measurement of strain and strain rates require a high quality echocardiogram machine, or rely on predictions made from tissue velocity measurements. Predictions of strain based on tissue velocity measurements, though they can be made using non-invasive ultrasound techniques, are not consistently accurate. Myocardial velocity measurements, furthermore, conventionally relate to net, or bulk, tissue movement. Continuous measurement of contractility over a prolonged period of time using echocardiogram techniques is not practical or cost effective, especially in an intensive care unit or operating room, where it may be desirable to monitor many patients simultaneously.

Methods and systems of the present invention provide determinations of strain rate as the rate of change of strain, measured directly using non-invasive ultrasound techniques over time. Strain rate is measured, not as bulk movement of myocardial tissue but, rather, as relative movements of selected target sites within myocardial tissue. And, because the time of peak strain rate is evanescent, improvements in accuracy of peak strain measurements provided using methods and systems of the present invention, reduce the amount of necessary time averaging of the signal, and improve the cycling rate of the measurement. Both passive and active modes of the present invention may be implemented to determine strain in myocardial tissue. Moreover, the improved accuracy, non-invasiveness and cost-effective attributes of methods and systems of the present invention permit use of strain and strain rate measurements for monitoring myocardial contractility and tissue properties, as well as diagnosis of myocardial dysfunction.

Myocardial Ischemia and Infarction

Tissue Doppler ultrasound techniques have been used to detect myocardial ischemia, primarily in experimental situations that involve severe ischemia and consequent impairment of systolic dysfunction. Strain rate patterns change dramatically with the onset of ischemia, characterized by a delayed onset of (contraction) strain rate, decreased peak systolic strain rate and strain, post-systolic shortening, and decreased peak strain rate during early ventricular filling. See, e.g., Pislaru C, Anagnostopoulos P D, Seward J B et al.: Higher myocardial strain rates during isovolumic relaxation phase than during ejection characterize acutely ischemic myocardium, J Am Coll Cardiol 2002; 40:1487–1494. The magnitude of infarction can be determined as well when the myocardium is exposed to dobutamine. Transmural infarction (total infarction) is identified by an almost complete absence of strain rate or integrated strain over the cardiac cycle, whereas incomplete infarction demonstrates reduced strain and strain rate at rest, and progressive post-systolic increases in strain (post-systolic shortening) in response to dobutamine. See, e.g., Weidemann F, Dommke C, Bijnens B et al.: Defining the transmurality of a chronic myocardial infarction by ultrasonic strain-rate imaging, Circulation 2003;107:883–888. The use of dobutamine stress, in combination with strain rate analysis, appears to be the best method to assess how much myocardial tissue remains alive after a myocardial infarction. See, e.g., Hoffmann R, Altiok E, Nowak B et al: Strain rate measurement by doppler echocardiography allows improved assessment of myocardial viability in patients with depressed left ventricular function. J Am Coll Cardiol 2002; 39:443–449. Using PET scanning to define the degree of viable tissue in areas of myocardium that had suffered infarction, viable tissue demonstrated increases in strain rate to dobutamine whereas non-viable tissue did not. Prediction of viability from strain rate was better than standard 2-D echo analysis of wall motion and better than examination of tissue velocities alone.

Although determinations of strain rate may be made adequately using the current methods of tissue Doppler, the clinical detection of myocardial ischemia is suboptimal at present. In emergency rooms and intensive care units, ischemia is often not detected unless the patient complains of chest pain, or ECG changes happen to be noted. In the operating room, ECG detection of myocardial ischemia is really the only option, since most patients are asleep. Unfortunately, ECG changes are often a late event in ischemia.

2-D echocardiography can detect ischemia via decreases in regional systolic wall motion, but the cost (of the machine and the operator) limits the extent to which this method can be used in routine clinical settings.

Methods and systems of the present invention that provide direct measurement of tissue properties, such as stiffness, tension, strain, etc., using non-invasive ultrasound techniques, are well suited for early detection of myocardial ischemia and infarction. Myocardial tissue properties determined using acoustic techniques may be used, for example, to monitor diastolic relaxation, which is often the first clinical indication of cardiac ischemia.

Ventricular Filling and Atrial Pressures

The degree of ventricular filling has important ramifications for management of the heart and heart function in virtually all critical care situations, including the intensive care unit and the operating room. There are two clinical issues that must be dealt with: the amount of blood in the ventricle (end-diastolic volume); and the pressure in the left atrium. These two are related, as ultimately the pressure in the atrium is responsible for pushing blood into the ventricle. However, the relationship is curvilinear and may shift (for the same ventricular blood volume) to higher or lower filling pressures, depending on the stiffness of the myocardium that is, in turn, influenced by many factors including tissue injury and diastolic function.

The blood volume of the ventricle is important, because the heart cannot pump what it does not have. Without blood entering the ventricle, there is no cardiac output and no blood pressure. Furthermore, the strength of the ventricular contraction is in part dependent on the stretch of the myocytes at the initiation of contraction. Greater stretch, produced by greater blood volume, generally increases the strength of the contraction. Volume can be estimated non-invasively by 2-D echocardiography, but the cost of the equipment makes it difficult to obtain multiple measurements over the course of a day, let alone to monitor blood volume continuously. Currently, central venous or pulmonary wedge pressure is often used to estimate ventricular end-diastolic pressure, but the interpretation of the value is problematic due to the curvilinear relationship between pressure and volume. This problem is particular true in the early part of the curve, where large changes in ventricular volume may have only small effects on end-diastolic ventricular and atrial pressure.

Using methods and systems of the present invention involving observation of the intrinsic and/or induced acoustic properties of myocardial tissue, such as stiffness, tension, etc., are measured to determine ventricular filling and/or volume. As the ventricle fills, radius increases and wall thickness decreases. Therefore, even if end-diastolic pressure changes minimally, increased volume results in increased tension. In fact, the myocardial tension changes more than pressure as the ventricle expands thereby making tension a better measure of volume status than pressure alone. Techniques that predict tissue strain rate, and/or strain based on tissue velocity determinations are generally not suitable for making ventricular filling and/or volume predictions, because they don't directly determine a zero tension point at the beginning of diastole. The ability to measure absolute myocardial strain, using methods and systems of the present invention, permits the utilization of myocardial strain as an index of ventricular volume.

Even if atrial pressure is not used to estimate ventricular volume, atrial pressure is still an important clinical parameter. Whatever the atrial pressure, it must be exceeded by the veins taking blood to the atrium. If the back-pressure gets too high, then fluid leaks out of the upstream veins and capillaries and can lead to clinical problems such as anasarca, liver dysfunction and pulmonary congestion or edema, all of which can be life-threatening. Thus, when a clinician attempts to optimize ventricular filling, the clinician must also be cognizant of the impact higher atrial pressures might have on the body. As direct measurement of central venous or pulmonary artery wedge pressures requires an invasive catheter, attempts have been made to estimate wedge pressure with non-invasive echocardiographic techniques. The technique that utilizes tissue Doppler involves calculating the E/Ea ratio, where E is the peak blood inflow rate across the mitral valve in early diastole and Ea is the peak tissue velocity in early diastole as measured at the mitral annulus (Sengupta et al, 2002). It is believed that wall tension measurements and their rate of change may prove as useful as Ea or even the E/Ea ratio.

Diastolic Dysfunction

Diastolic dysfunction involves slowed and even incomplete relaxation of the ventricle during diastole. The functional implication is that if the ventricle remains stiff, particularly in early diastole when it is supposed to be receiving rapid inflow of blood from the atrium, then either too little blood will enter the ventricle, or the pressure in the atrium will have to increase to force the blood into the ventricle. If the atrial pressures increase to unacceptably high values, then signs and symptoms of fluid overload develop. In patients with known diastolic dysfunction but normal systolic function, alterations are observed in diastolic tissue velocities. The ratio of myocardial velocity at the annulus in early diastole (Em) to that in late diastole (Am) has been applied in much the same manner that the E/A ratio of blood flow across the mitral valve has been used to detect diastolic dysfunction (Isaaz, 2002). There is evidence that Em itself reflects diastolic relaxation and is not affected by the atrial pressure, making it more useful than the E/A ratio. When peak strain rates in diastole are measured, they are reduced in early diastole (Stoylen, 2001).

Although these velocity measurements show promise, they are still relatively indirect measurements of how fast the ventricle is relaxing during the isovolumic relaxation phase of the cardiac cycle and early diastolic filling. The "gold standard" for assessment of diastolic relaxation is the rate of decay of ventricular pressure during isovolumic relaxation (expressed as the time constant, tau, of ventricular pressure relaxation) (Mandinov, 2000). Of course, this measurement is highly invasive as it requires a catheter in the ventricular chamber. The rate of decrease of myocardial wall tension during isovolumic relaxation should mimic the decay of ventricular chamber pressure. Myocardial velocity in early diastolic filling (Em) correlates with tau and, like tau, appears to be little affected by loading conditions (atrial pressure, aortic pressure) (Waggoner, 2001). Therefore strain rate in early diastolic filling may not be affected by loading conditions, and so prove to be a useful measure of diastolic relaxation, too. Furthermore, the time trace of absolute tension near the tension nadir may reflect how quickly the myocardium relaxes.

The concept that the tension wave can be accurately determined over time, especially during isovolumic relaxation and early diastole, has the potential to characterize uniquely a wide range of disorders. Constrictive and restrictive pericariditis and cardiomyopathies have distinctive patterns of pressure in the ventricular chamber. If tension follows the same pattern as pressure, then tension measurements could easily accomplish what currently requires invasive measurement. Graded myocardial ischemia, as opposed to abrupt total occlusion of coronary artery blood flow, may first present as diastolic dysfunction and therefore precede ECG changes and even changes in systolic function. Thus, if a system can monitor both diastolic and systolic function, that system has the most chance of detecting ischemia early and provide the physician a greater opportunity for intervention before the condition worsens. As with all applications, assessment of diastolic function may be accomplished using either the passive or active ultrasound modes of the present invention, or both modes simultaneously or alternately.

Acoustic detection techniques that involve the application of acoustic interrogation signals to a target tissue site and acquisition of acoustic scatter data are preferred, but alternative detection techniques, including near-infrared spectroscopy (NIRS), optical coherence tomography (OCT), magnetic resonance techniques, positron-emission tomography (PET), acoustic hydrophones and the like, may be used. A portable, relatively low-cost magnetic resonance scanner is described, for example, in the California Institute of Technology Engineering and Science publication, Vol. LXIV, No. 2, 2001. The use of these techniques to measure various spatial and temporal aspects of tissue deformation and associated biological responses is generally known.

Ultrasound sources and detectors may be employed in a transmission mode, or in a variety of reflection, palpation or scatter modes, including modes that examine the transference of pressure waves into shear waves, and vice versa. Ultrasound detection techniques may also be used to monitor the acoustic emission(s) from insonified tissue. Detection techniques involving measurement of changes in acoustic scatter, particularly backscatter, or changes in acoustic emission, are particularly preferred for use in methods and systems of the present invention operating in either the passive or active modes, or in both modes simultaneously or alternately. Exemplary acoustic scatter or emission data that are related to tissue properties include: changes in scatter or acoustic emission, including changes in the amplitude of acoustic signals, changes in phase of acoustic signals, changes in frequency of acoustic signals, changes in length of scattered or emitted signals relative to the interrogation signal, changes in the primary and/or other maxima and/or minima amplitudes of an acoustic signal within a cardiac and/or respiratory cycle; the ratio of the maximum and/or minimum amplitude to that of the mean or variance or distribution of subsequent oscillations within a cardiac cycle, changes in temporal or spatial variance of scattered or emitted signals at different times in the same location and/or at the same time in different locations, all possible rates of change of endogenous tissue displacement or relaxation, such as the velocity or acceleration of displacement, and the like. Multiple acoustic interrogation signals may be employed, at the same or different frequencies, pulse lengths, pulse repetition frequencies, intensities, and the multiple interrogation signals may be sent from the same location or multiple locations simultaneously and/or sequentially. Scatter or emission from single or multiple interrogation signals may be detected at single or at multiple frequencies, at single or multiple times, and at single or multiple locations.

Acoustic properties of scatter and/or emission data from selected target tissue site(s), or derivative determinations such as tissue displacement, tissue stiffness, and the like, are related, using empirical formulations and/or mathematical models, to tissue properties and/or clinical parameters. The relation of acoustic properties may be used in combination with other parameters, such as blood pressure, to assess tissue properties and/or clinical parameters. In one example, declining blood pressure during surgical procedures may indicate either diminished or elevated fluid volumes. Blood pressure may be monitored concomitantly with the acoustic properties of targeted cardiac tissue to determine whether declining blood pressure is a result of diminished or elevated fluid volumes. In general, increases in cardiac wall stiffness provide evidence of elevated fluid volumes, while reductions in cardiac tissue stiffness provide evidence of reduced fluid volumes.

Single or multiple interrogation signals administered from different places and/or at different times may insonify single or multiple target tissue sites. Intrinsic and/or induced acoustic properties of the insonated target tissue may be assessed, by acquiring scatter or emission data, simultaneously and/or sequentially. One of the advantages of the methods and systems of the present invention is that target tissue sites may be volumetrically small, and spatially resolved, to provide data from localized tissue sites with a high degree of spatial resolution. In this way, localized differences in tissue properties may be identified and associated with a spatial location within the interrogated tissue. According to one embodiment, tissue sites of varying size and/or location are assessed simultaneously or sequentially. For most applications, the use of acoustic source(s) and/or transducer(s) capable of interrogating and detecting target tissue sites having a volume of from 1 $mm^3$ to 100 $cm^3$ are suitable.

For assessment and/or monitoring of cardiac tissue properties based on the acoustic properties of tissue, the target tissue site is preferably at a selected site within or on a surface of cardiac tissue. For many applications, the ventricle or atrium walls are targeted; for some applications, for example, the right ventricular wall is targeted. Assessment of cardiac tissue properties based on their intrinsic and/or induced acoustic properties may be supplemented with data relating to mean and/or continuous arterial blood pressure, cardiac cycle information, heart rate, and the like.

Determinations of mean and/or continuous arterial blood pressure may be made, using ultrasound according to methods and systems of the present invention, in parallel with determinations of cardiac tissue properties and parameters. Blood pressure determinations may be made, for example, by selecting a target tissue site within or on or in proximity to a blood vessel and, preferably, in proximity to cardiac tissue. In this way, a single, integrated acoustic system may be used for making determinations of mean and/or continuous arterial blood pressure in parallel with determinations of cardiac tissue properties and parameters.

In yet another aspect, noninvasive systems and methods of the present invention provide a measure of arterial or venous blood pressure using acoustic techniques to measure alternating compression and dilation of the cross-section or other geometric or material properties of an artery or vein, using empirically established relationships and/or mathematical models. In another aspect, blood pressure is determined using acoustic techniques to measure alternating compression and dilation of tissue surrounding blood vessels that is displaced as the vessels are compressed and dilated with the cardiac cycle. Geometrical properties that may be determined using acoustic detection techniques include changes in diameter, cross-sectional area, aspect ratio, rates of changes in diameter, velocity, and the like. Material properties that may be determined using acoustic detection techniques include the stiffness of vessel walls or tissue in proximity to vessel walls. Blood pressure may be assessed, for example, by acquiring acoustic data, in an active and/or passive mode, from target tissue sites at or in proximity to one or more blood vessels. The acoustic data can be related to the stiffness of vessel walls or supporting tissue, which can be related to blood pressure. Suitable target tissue sites for determination of arterial or venous blood pressure may comprise any blood vessel or surrounding tissue. Detection of ultrasound scatter data may be related, for example, with synchronous Doppler flow measurements within the same vessel.

A calibration step using a measure of blood pressure taken with a conventional blood pressure device, may be incorporated in the blood pressure determination. Acoustic proxies for the pulsatility of the blood vessel—such as oscillation rate of the blood vessel wall—may be substituted for direct measures of those quantities. In this method, the spontaneous changes in the diameter (or other geometric property) of the vessel being monitored are assessed using ultrasound, and this information is related (e.g., using correlation techniques) to synchronous Doppler flow measurements within the same vessel. Since the diameter (or other geometric property) of the vessel is a function of the pressure being exerted against the wall of the vessel by blood, and since the velocity of blood flow is dependent on the diameter (or radius) of the vessel through which the blood travels, blood pressure can be calculated from flow velocity measured by Doppler. By simultaneously measuring the pulsatility of the blood vessel of interest and the Doppler flow velocity proximal and distal to this site, continuous blood pressure can be determined.

In one embodiment, described in detail below, an acoustic detector, such as an ultrasound transducer, detects ultrasound signals that are indicative of tissue displacements, or associated biological responses, in one or more of the following operating modes: transmission, reflection, scatter, emission, backscatter, echo, Doppler, color Doppler, harmonic, subharmonic or superharmonic imaging, a-mode, m-mode, or b-mode. Ultrasonic interrogation pulses having a known frequency, intensity and pulse repetition rate are administered to a desired target tissue site. The intensity, frequency and pulse repetition rates of the ultrasonic interrogation pulses are selected such that the interrogation pulses do not produce undesired side effects, and do not substantially interfere with intrinsic tissue displacements resulting, for example, from blood flow and respiration. Transmitted signals, signal reflections, acoustic emissions, scatter such as backscatter, and/or echoes of the interrogation pulses are detected and used to assess intrinsic tissue displacements and/or tissue properties at the target tissue site. In preferred embodiments of the passive assessment mode, an acoustic detector is implemented to detect the backscatter of administered interrogation signals. An acoustic detector may additionally or alternatively be operated in a Doppler mode to measure the phase shift of ultrasound reflected back to the detector.

A variety of techniques may be used to analyze the acquired acoustic data relating to intrinsic and/or induced cardiac tissue displacement or associated biological responses. For example, analytical techniques developed and employed in connection with ultrasound imaging, such as cross-correlation, auto-correlation, wavelet analysis, Fourier analysis, CW Doppler, sum absolute difference, and the like, may be employed to determine various properties of tissue deformation, and to relate tissue deformation to tissue properties. Other empirical techniques and systems, such as artificial neural networks (ANNs), linear filters (including those with both infinite impulse response IIR and finite impulse response FIR properties), Hidden Markov Models (HMMs), heuristics and fuzzy logic systems, may be used to relate one or more variables, such as tissue deformation, displacement, ABP, etc., to desired cardiac tissue properties and cardiac parameters. False peak correction techniques may be used to improve the accuracy of the assessment. Additionally, properties of the major and minor endogenous oscillations of cardiac tissue within a cardiac cycle, or relationships between major and minor endogenous oscillations within a cardiac cycle, or across several respiratory cycles, may be empirically related to cardiac tissue properties and conditions. These determinations may be made with, or without, additional information relating to ABP and/or respiration and/or exogenous tissue displacements. In one embodiment, parameters such as ABP are measured using other techniques, and one or more externally measured parameters are used for calibrating determinations made by systems of the present invention.

Methods and systems of the present invention are preferably integrated with control and data storage and manipulation features similar to the control and data storage and manipulation features provided on other types of diagnostic and monitoring systems. Various types of control features, data storage features, data processing features, data output features, and the like, are well known in the art and may be adapted for use with the present invention.

Various modes of operation of methods and systems of the present invention are described below and in the description of preferred embodiments.

First "Active" Acoustic Probing or Palpation Mode

In a first "active" mode, methods and systems of the present invention stimulate or probe target cardiac tissue, or induce a response at a target cardiac tissue site, by application of focused ultrasound. The response of the targeted tissue to the application of focused ultrasound may be deformation or displacement (a change in relative position), a change in temperature, a change in blood flow, or another detectable response. For example, application of an acoustic radiation force to "palpate" a target cardiac tissue site may be accomplished by administering one or more acoustic signals. Non-invasive techniques, such as ultrasound, optical techniques such as near infrared spectroscopy and optical coherence tomography, and other techniques, including magnetic resonance techniques, external electrophysiological stimulation, patient response, and the like are used to assess at least one response to the application of focused ultrasound. A visualization or imaging technique, such as ultrasound imaging or magnetic resonance imaging, may also be employed to assist in targeting the focused ultrasound pulse(s) and to assist in differentially localizing responsive tissues.

Acoustic techniques, such as ultrasound, may be used to induce biological responses in tissue and to deflect or deform biological materials. Biological materials absorb some of the ultrasound as it propagates into and through the material. See, e.g., Rudenko et al. (1996), "Acoustic radiation force and streaming induced by focused nonlinear ultrasound in a dissipative medium," J. Acoust. Soc. Am 99(5) 2791–2798. Also, at the boundaries between different tissue types, there is an 'impedance mismatch' (that is, differences between the product of density and speed of sound from one tissue to another) that allows ultrasound to push on the interface. See, e.g., Chu and Apfel (1982) "Acoustic radiation pressure produced by a beam of sound," J. Acoust. Soc. Am 72(6), 1673–1687.

For assessment of cardiac tissue and assessment of cardiac parameters, for example, one or more acoustic transducer(s) is placed in contact with or in proximity to a subject's chest. An initial environmental assessment, described below and preferably employing ultrasound techniques, may be made, if desired, to assess the characteristics of the environment between the acoustic source and the target tissue site, so that the magnitude of the acoustic force applied to the target tissue may be determined. Environmental factors, such as the distance between the acoustic transducer and various structural landmarks, may be determined. An initial environmental assessment may be determinative of various method and system parameters. Environmental assessments may additionally be updated at intervals throughout a diagnostic or monitoring procedure.

Following the (optional) environmental assessment, an acoustic force is applied by an acoustic transducer, at a predetermined frequency, to displace targeted cardiac tissue at a targeted location. The deformation may be produced at any desired location within cardiac tissue, depending on the focus (foci) of the ultrasonic transducer(s) producing the acoustic radiation force. In some systems, variable foci ultrasonic transducers are provided, and a diagnostic procedure is carried out using a plurality of target tissue sites. According to one embodiment for assessment of cardiac output, the focus (foci) of the ultrasonic transducer(s) is preferably provided in proximity to the surface or a small distance below the surface of a ventricle wall, to maximize the tissue displacement induced by the radiation pressure that arises from the impedance mismatch between cardiac tissue and fluid.

The applied acoustic radiation force is sufficient to induce a detectable displacement in the cardiac tissue, or the applied ultrasound beam is sufficient to produce a detectable biological response, without producing any medically undesirable changes in the examined tissue. For example, the acoustic radiation force applied must not produce shear in tissues in proximity to the target tissue of a magnitude sufficient to tear or damage tissue. The applied ultrasound, moreover, must not appreciably increase the temperature of examined tissue to the point of causing unacceptable damage, and it must not induce extensive or damaging cavitation or other produce other deleterious mechanical effects in the examined tissue. Suitable ultrasound dosages may be determined using well known techniques. For example, Fry et al. studied the threshold ultrasonic dosages causing structural changes in mammalian brain tissue and illustrate, in their FIG. 1, the acoustic intensity v. single-pulse time duration producing threshold lesions in white matter of the mammalian (cat) brain. Fry et al., *Threshold Ultrasonic Dosages for Structural Changes in the Mammalian Brain*, The Journal of the Acoustical Society of America, Vol. 48, No. 6 (Part 2), p. 1413–1417 (1970). One of ordinary skill in the art may routinely determine safe ultrasonic dosages for application to cardiac tissue.

Additionally, the acoustic frequency must be low enough to penetrate the tissues between the skin surface and the cardiac tissue, and high enough to produce measurable deformation in the target tissue at the location of interest. Within the parameters outlined above, higher frequency acoustic waves are more easily focused and, therefore, are preferred. The intensity must be high enough to deform the tissue, but not be so great as to induce undesirable changes in the examined tissue. The pulse length is preferably relatively short, but long enough to create a measurable deformation or oscillation of the target tissue, as desired, while the pulse repetition frequency must be large enough to resolve medically interesting temporal features in the tissue, without inducing medically unacceptable changes in the tissue.

In general, at least one acoustic property related to tissue displacement, or an associated biological response, is determined and related to a tissue property and, ultimately, to a clinically important parameter. For example, the magnitude, or amplitude, of the displacement induced by the known acoustic force is directly related to the elasticity (or stiffness or compliance, e.g., Young's modulus) of the cardiac tissue, and can therefore be empirically related to clinically relevant cardiac parameters, such as cardiac output. Additional properties of the target tissue displacement that may be determined and related to tissue properties include: various components of amplitude, such as maximum amplitude in the direction of the acoustic force or maximum amplitude perpendicular to the direction of acoustic force; all possible rates of change of the displacement or subsequent relaxation of the tissue, such as the velocity or acceleration of displacement or relaxation; the amplitude or rates of change of various components of the shape of the displacement; changes in Fourier or wavelett representations of the acoustic scatter signal associated with the displacement; properties of shear waves generated by the acoustic radiation force; properties of induced second harmonic deformation(s), and the like. Time displacements of pulse echoes returning from the target tissue are also indicative of the displacement amplitude and may be determined. These properties are all referred to as measures of "displacement."

Second "Active" Acoustic Probing or Palpation Mode

In a second "active" mode of operation, application of focused ultrasound produces oscillation of targeted tissue, and data relating to the acoustic signals emitted from the targeted tissue are collected. These signals are referred to herein as acoustic emissions. In general, methods and systems of the present invention that relate to application of focused ultrasound may be used to produce oscillation of targeted tissue, and emitted acoustic signals are related to tissue properties and physiological conditions.

In one embodiment, methods and systems of the present invention employ a confocal acoustic system comprising at least two acoustic transducers, driven at different frequencies, or a focal acoustic system comprising a single acoustic transducer driven at a given pulse repetition frequency (PRF), to induce an oscillatory radiation force in the target tissue, such as cardiac tissue. The resulting oscillation is at a frequency that is the difference of the applied frequencies, at the target location that is marked by the overlap of the two confocal acoustic beams or, for the single transducer case, at the PRF. During and after the application of focused ultrasound, the targeted tissue emits acoustic signals related to its intrinsic properties. The second, active mode of operation may therefore be used to characterize tissue. Diagnostic ultrasound techniques may be used to measure the frequency or other properties of the emitted acoustic signal, which are empirically related to tissue properties.

"Passive" Acoustic Mode

In a "passive" acoustic mode, methods and systems of the present invention employ acoustic techniques, such as ultrasound, to acquire data relating to intrinsic (endogenous) tissue displacements. Ultrasound backscatter and/or emission data, for example, are related to intrinsic tissue displacements, which can be related to various tissue properties. Supplemental data, such as measures of mean and/or continuous arterial blood pressure, blood flow, and the like, may additionally be used in these determinations.

For example, the magnitude or amplitude or phase of acoustic scatter from target cardiac tissue sites undergoing intrinsic displacements during the course of the cardiac cycle, is directly related to the stiffness, e.g. Young's modulus, of the cardiac tissue. Alternatively or additionally, relationships between the major and minor intrinsic oscillations of cardiac tissue within a cardiac cycle, or within a cardiac cycle as modulated by one or more respiratory cycles, are empirically related to tissue properties. Properties of the intrinsic tissue displacement that may be assessed and related to tissue properties include: various components of amplitude, such as maximum amplitude within a cardiac cycle, the ratio of the maximum amplitude to that of the mean or variance of subsequent oscillations within a cardiac cycle, all possible rates of change of intrinsic cardiac tissue displacement or relaxation, such as the velocity or acceleration of displacement, and the like. Additional data, such as ABP measurements and/or respiration data, may be collected and used, with the acoustic data, to make various assessments and clinical determinations.

Relative trend determinations of the target cardiac tissue properties, such as stiffness, contractility, tension, strain and the like, at or near the relevant portions of the heart (e.g. ventricle walls and/or atrium walls) are made during certain portions of the cardiac cycle, and may be synchronized with EKG measurements. In general, the right ventricle is relatively easy to image with ultrasound. We discuss assessment of cardiac parameters using the physical properties (e.g., tension) in the right ventricle wall as exemplary, though other cardiac target sites may be used. For some embodiments, data may be collected over many cardiac cycles, in some embodiments starting when the patient's ventricle wall tension is known to be normal, such as before or early in the time course of surgery, and continued until the patient is stabilized. In one embodiment, a system of the present invention comprises an inexpensive transducer with its own power supply, controller and display unit, designed to fit onto standard cardiac diagnostic ultrasound scan heads and interface electronically with standard diagnostic ultrasound machines. In another embodiment, one or more transducer array(s) are used for interrogation of and acquisition of acoustic data.

DETAILED DESCRIPTION OF THE INVENTION

Figure 1:
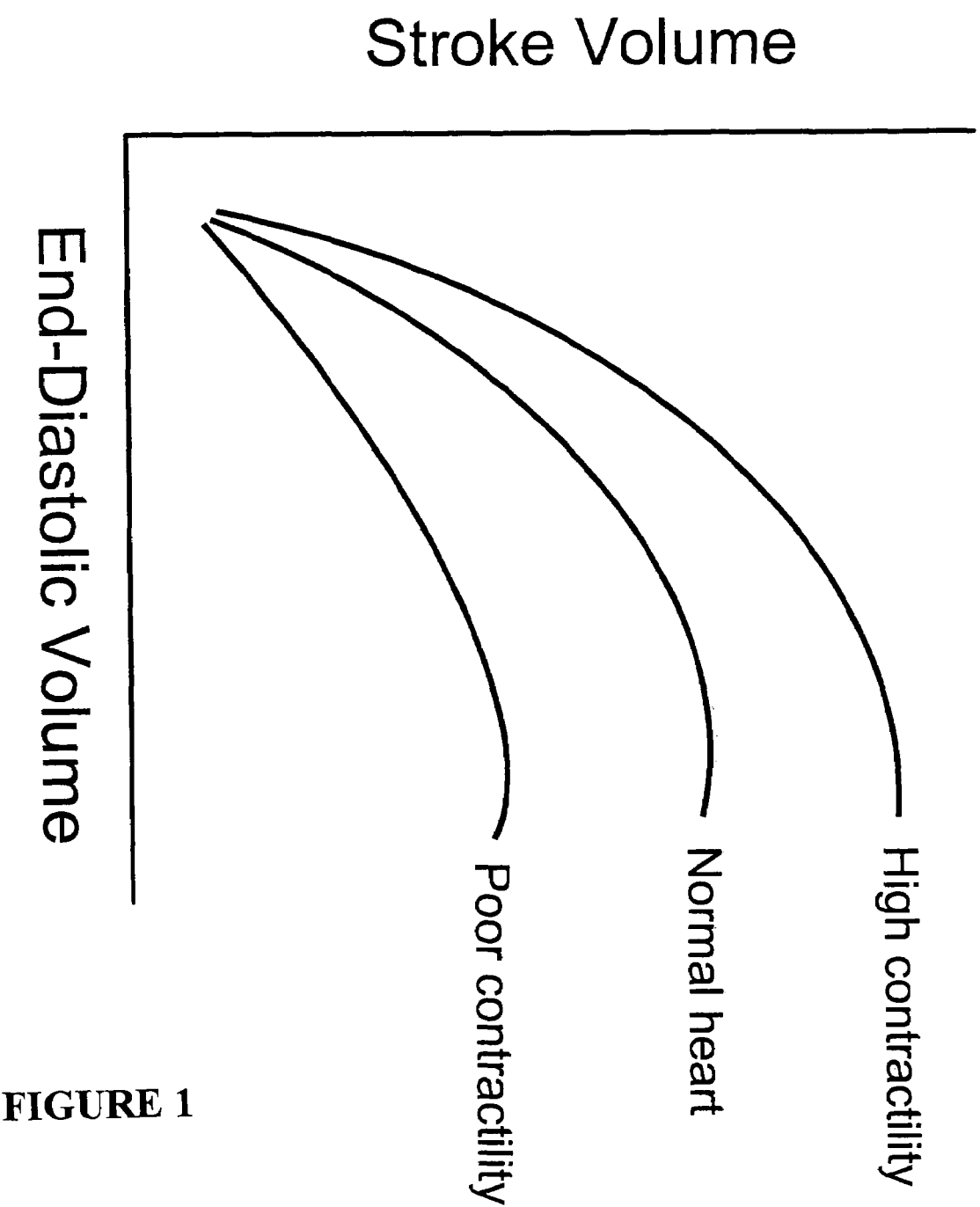
FIG. 1 shows the relationship between stroke volume and end-diastolic volume for normal cardiac tissue, as well as cardiac tissue that has high and poor contractility.
Figure 2:
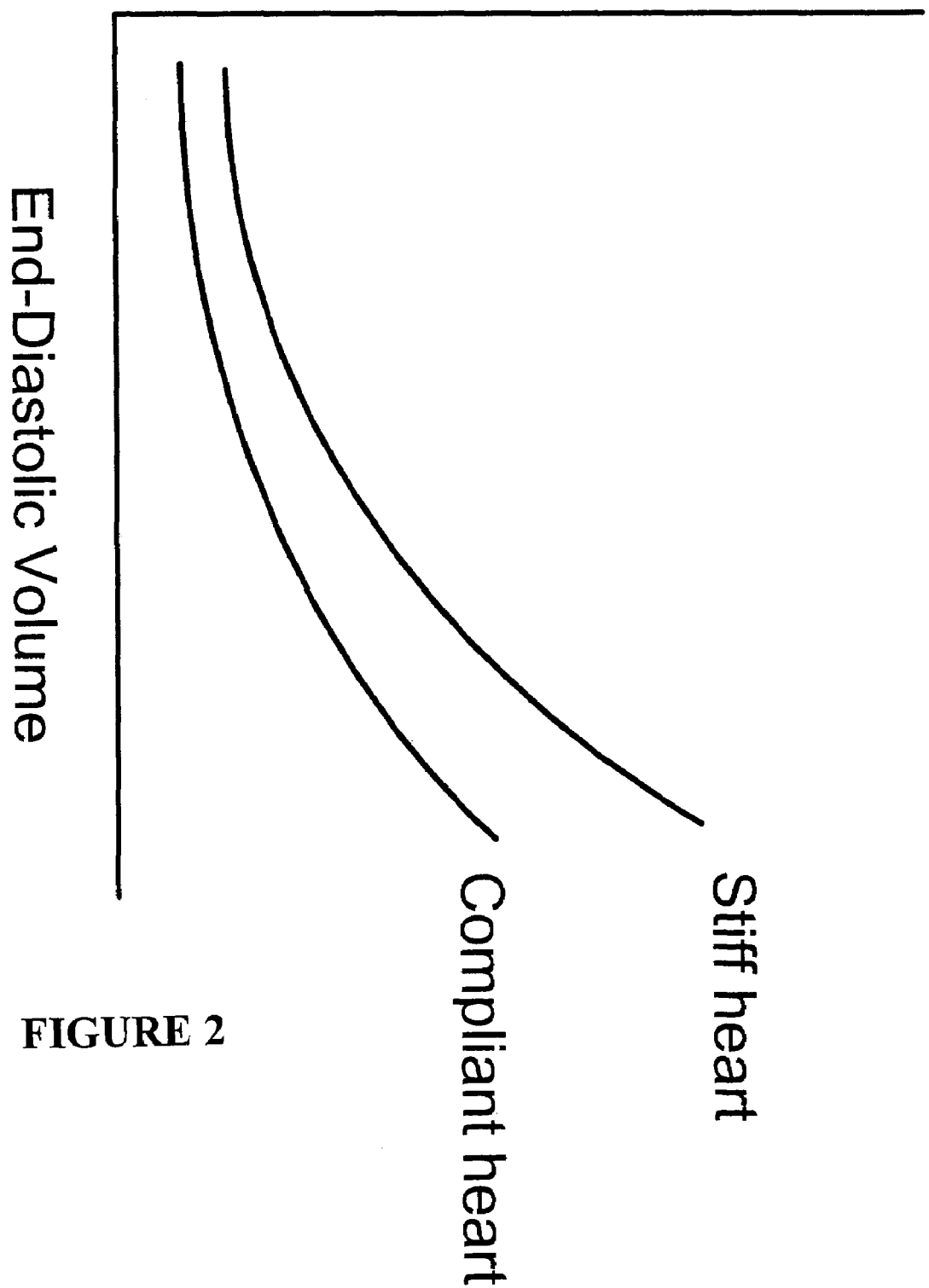
FIG. 2 shows the relationship between end-diastolic pressure and end-diastolic volume for stiff and compliant cardiac tissue.
Figure 3:
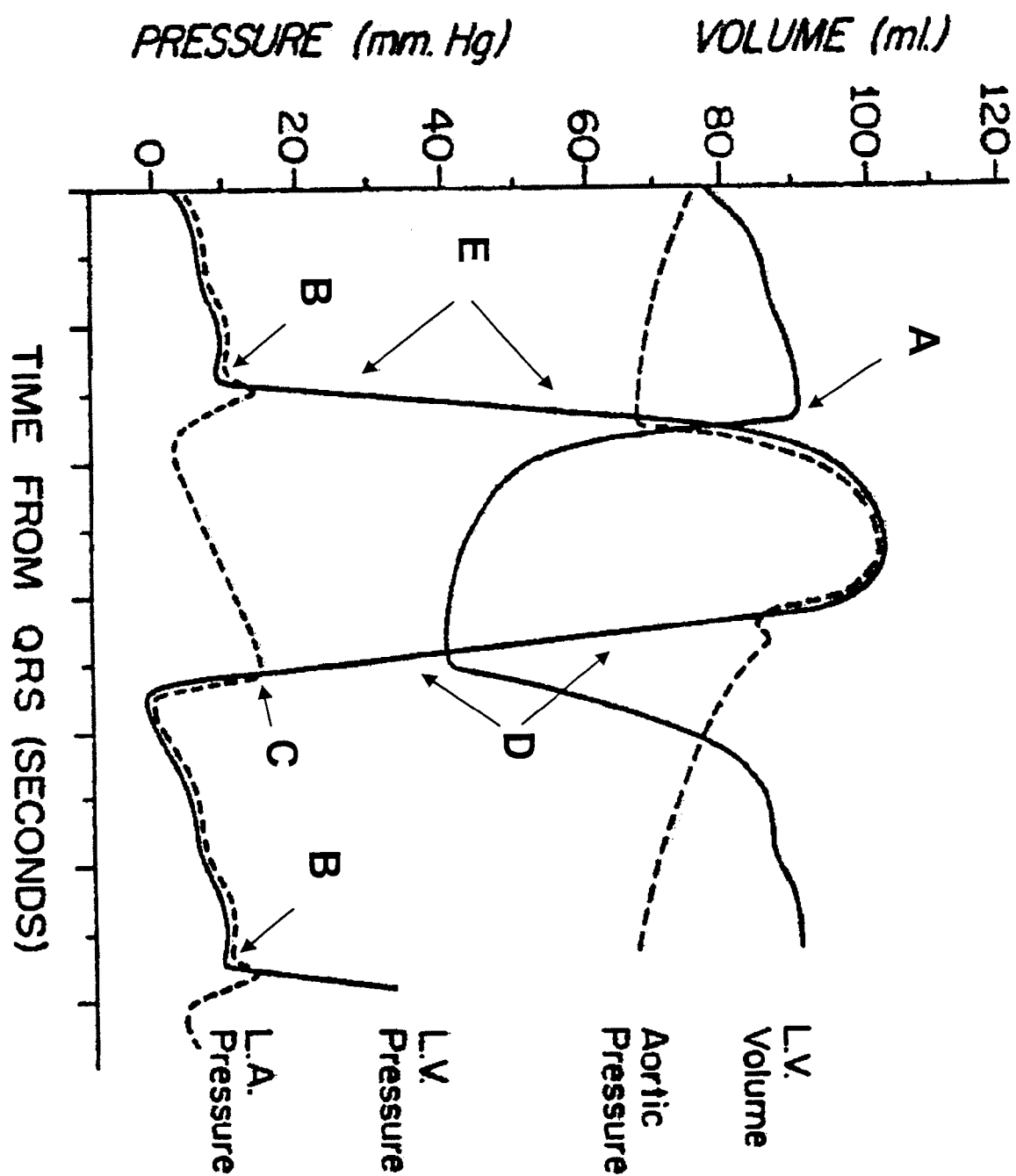
FIG. 3 shows the pressure and volume relationships during the cardiac cycle.
Figure 4B:
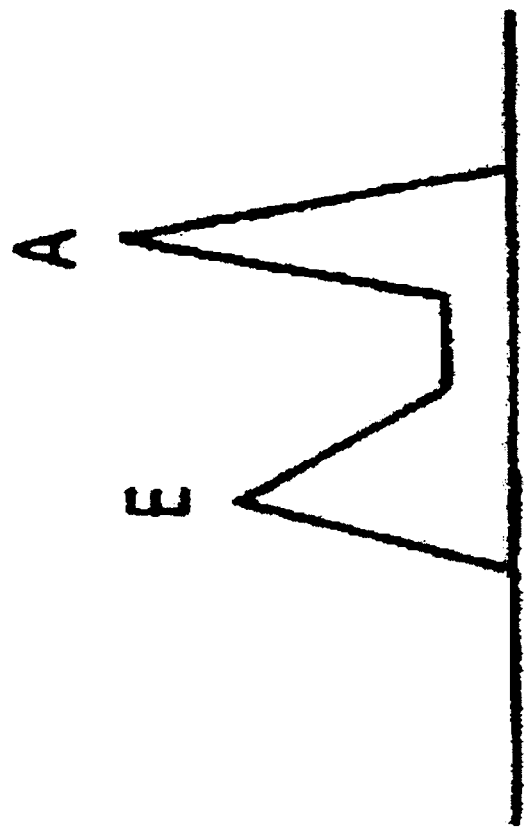
FIG. 4B illustrates abnormal ventricular filling profile, expressed in terms of volume over time, during a cardiac cycle.
Figure 4A:
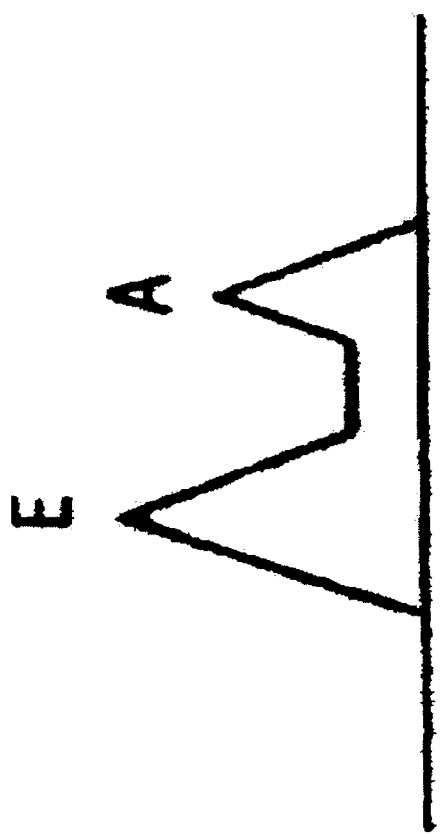
FIG. 4A shows a normal ventricular filling profile, expressed in terms of volume over time, during a cardiac cycle.
Figure 5:
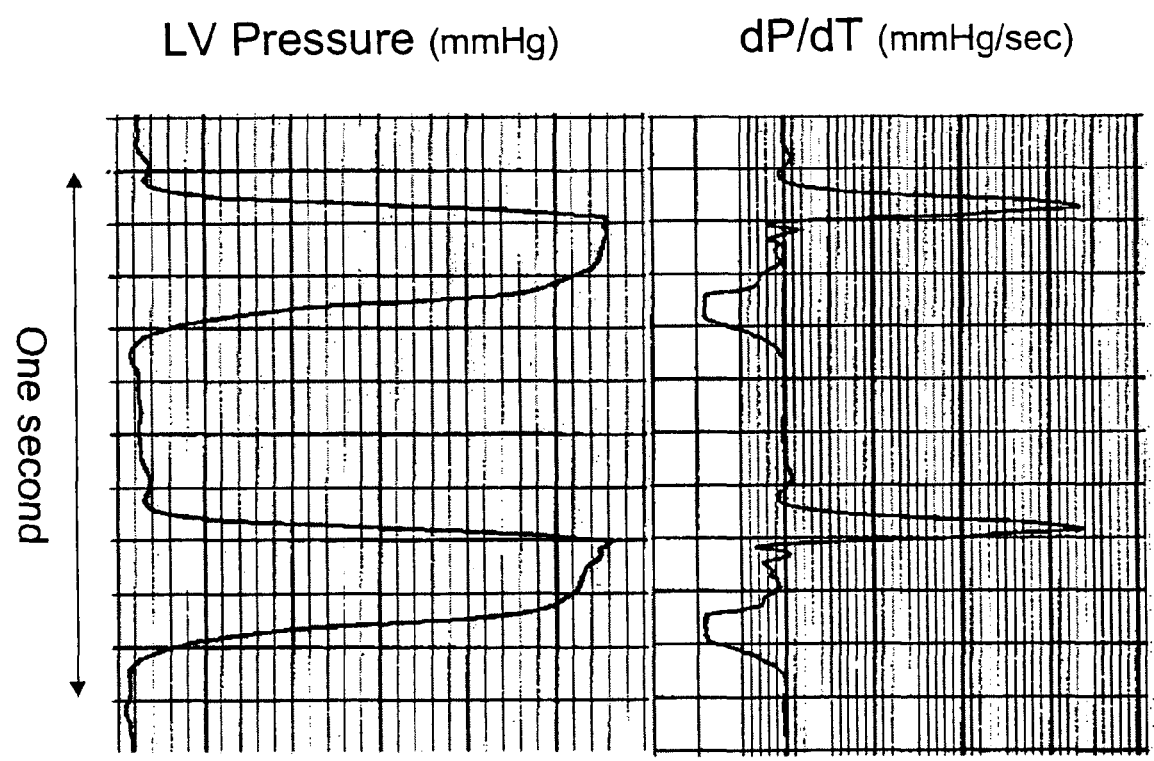
FIG. 5 shows a sample intraventricular pressure tracing (bottom panel) and the rate of change in pressure tracing (top panel).

While the methods and systems of the present invention may be embodied in a variety of different forms, the specific embodiments shown in the figures and described herein are presented with the understanding that the present disclosure is to be considered exemplary of the principles of the invention, and is not intended to limit the invention to the illustrations and description provided herein. In particular, preferred embodiments of methods and systems of the present invention are described with reference to assessment of cardiac tissue properties and cardiac parameters, such as cardiac output. It will be recognized by those having skill in the art that the methods and systems of the present invention may be applied to other cardiac tissue targets and, more broadly, to other types of cardiac tissue parameters.

Several exemplary systems of the present invention for acquiring data indicative of intrinsic and/or induced tissue displacements are described below. Although such systems may utilize commercially available components, the processing of the acquired data and the correlation of the acquired data to medically relevant physiological properties provides new modalities for noninvasively assessing numerous physiological parameters. Exemplary data processing techniques for detecting intrinsic and/or induced tissue displacements using acquired acoustic scatter data and correlating the acoustic scatter data or the displacement derivation with clinically important parameters, such as cardiac output, are also disclosed below. These techniques are exemplary and methods and systems of the present invention are not intended to be limited to the use of these exemplary techniques.

In a simplified system (not illustrated), a single acoustic transducer may provide the interrogation signal(s) required for tissue assessment in passive modes, the acoustic force required for tissue displacement in active modes, and additionally may provide for detection of scattered interrogation signal(s) that are indicative of intrinsic (passive mode) or induced (active mode) tissue displacement. For example, commercially available ultrasound transducers have sufficient bandwidth, such that a single transducer may be used to emit interrogation signal(s) for measuring intrinsic tissue displacements when operating at a first frequency, a first pulse repetition rate and a first intensity; to induce (exogenous) displacement or oscillation of tissue when operating at a second frequency, a second pulse repetition rate and a second intensity, and to detect signals reflected or backscattered or echoed or emitted from the tissue, e.g. when operated at a third frequency, or at additional frequencies, to assess the intrinsic or induced tissue displacement or emission, or to assess a biological response to the intrinsic or induced tissue displacement. Multiple acoustic transducers may also be used. In another embodiment, one or more diagnostic ultrasound probes and one or more displacement ultrasound probes may be embodied in a single acoustic element.

In general, acoustic interrogation pulses have larger peak positive pressure, have a higher frequency, and are shorter than acoustic palpation pulses. Acoustic interrogation pulses, for example, may have a typical frequency between 0.5 and 15 MHz, use from 1–50 cycles per pulse, consist of 3–10,000 pulses per second, and have a time-averaged intensity of less than 0.5 W/cm$^2$. Acoustic palpation signals may, for example, have a frequency of from 0.5 to 10 MHz, consist of long tone bursts of from 0.1–100 ms, consist of 1–100 pulses per second, and have a time averaged intensity of less than 100–1000W/cm$^2$, where longer pulses have lower intensities, for example. Acoustic emissions from palpated or oscillated tissue are expected to be in the frequency range of 500 Hz to 10 KHz.

Figure 6:
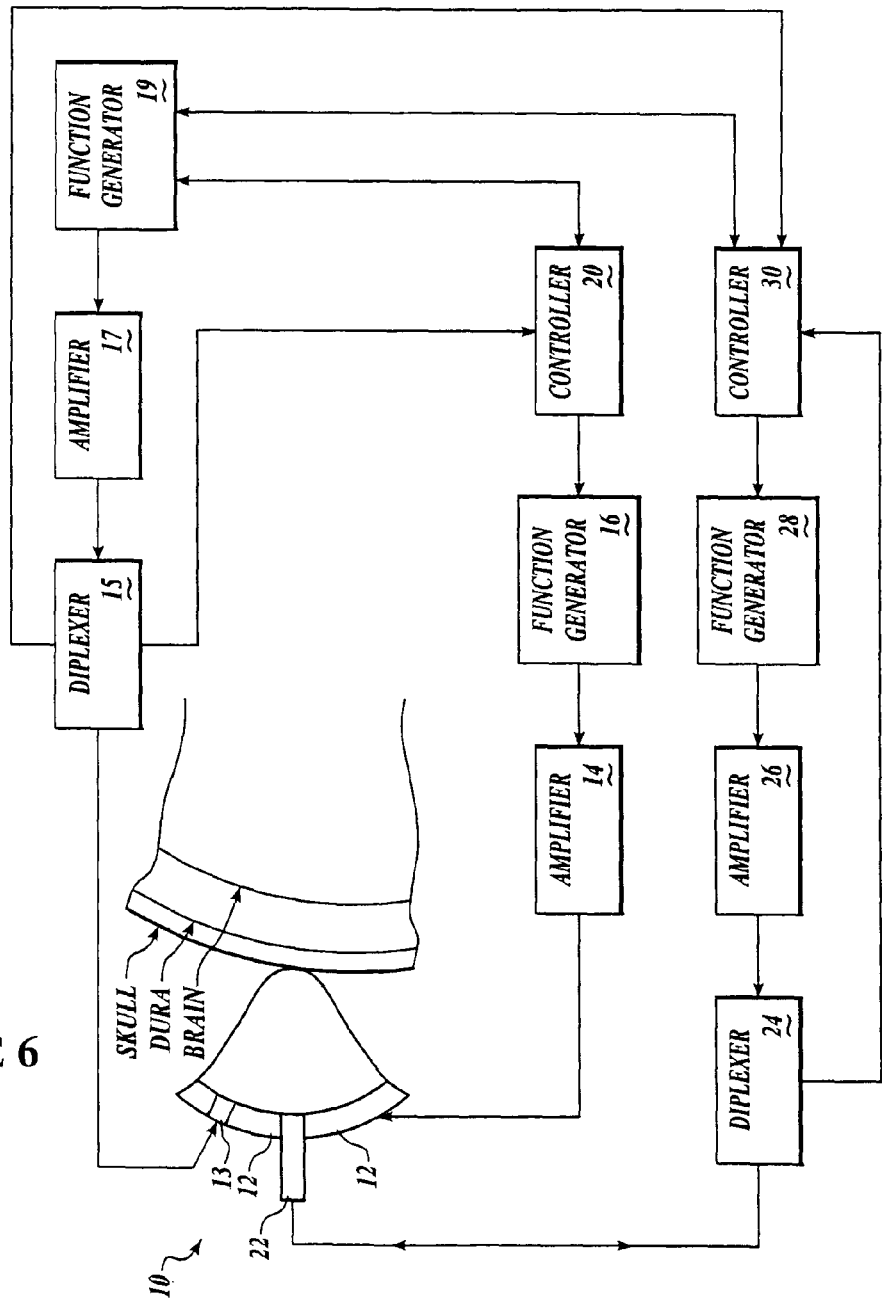
FIG. 6 is a schematic diagram illustrating a system of the present invention for inducing and detecting tissue deformation for assessing cardiac tissue properties.

FIG. 6 is a schematic diagram illustrating a system of the present invention for inducing and/or detecting at least one aspect of intrinsic or induced tissue displacement for applications such as assessment of cardiac tissue properties. As shown in FIG. 6, systems of the present invention comprise an acoustic source and receiver combination 10 for non-invasively assessing tissue displacement or emission at a distance from the source/receiver combination. In one embodiment suitable for use in passive modes to assess intrinsic tissue displacement, acoustic source and receiver combination 10 comprises one or more acoustic source(s) 12 for producing an interrogation signal. In another embodiment suitable for use in active modes to assess induced tissue displacement or emission, acoustic source and receiver combination 10 comprises one or more acoustic source(s) 22 for generating an acoustic radiation force, or for generating an oscillatory radiation force, or inducing an acoustic emission. Acoustic source(s) 12 are driven by and operably connected to an amplifier or power source 14, which is operably connected to one or more function generator(s) 16, which is operably connected to a controller 20. Controller 20 preferably has the capability of data acquisition, storage and analysis.

Controller 20, function generator 16 and amplifier 14 drive acoustic source(s) 12 in an interrogation (passive) or an acoustic radiation force (active) mode. In the passive mode, controller 30, function generator 28 and amplifier 26 drive acoustic source(s) 22 through the diplexer 24 at a desired frequency, intensity and pulse repetition rate to produce an interrogation signal for tissue target 32, such as cardiac tissue, without producing undesired side effects, and without producing a significant (exogenous) displacement. The resulting scattered signal is received at controller 30 via diplexer 24. In the active mode, controller 20, function generator 16 and amplifier 14 drive acoustic source(s) 12 at a desired frequency, intensity and pulse repetition rate to produce a displacement in tissue target 32, such as cardiac tissue, without producing undesired side effects. In some embodiments, the controllers 20 and 30 communicate with one another to interleave their signals in time, for example. The system based on transducer 22 can monitor the displacements and/or emissions induced by transducer 12.

The operating acoustic parameters are related to one another and suitable operating parameters may be determined with routine experimentation. The focal point of the acoustic source(s), or transducer(s), may be fixed and non-adjustable as a consequence of the mechanical configuration of the transducer. Alternatively, multiple transducers may be provided and arranged to permit variation and adjustment of the focal point. Acoustic sources, or transducers, are preferably annular in configuration and, in preferred embodiment, acoustic source 12 comprises multiple annular transducers arranged in a concentric configuration. Acoustic sources and tranducers may be arranged axially or off-axis with respect to one another.

A second acoustic source 13 driven by and operably connected to a diplexer 15, which is operably connected to an amplifier or power source 17, which is operably connected to a function generator 19, which, in turn, communicates with controller 20 and/or controller 30 may also be provided, as shown in FIG. 6. Acoustic source 13 may be used for assessing the characteristics of the environment between the acoustic source(s) and the target tissue, and may operate independently of transducer 12 and the related driver and controller components used for the assessment of the target tissue, or in coordination with transducer 12.

Figure 7:
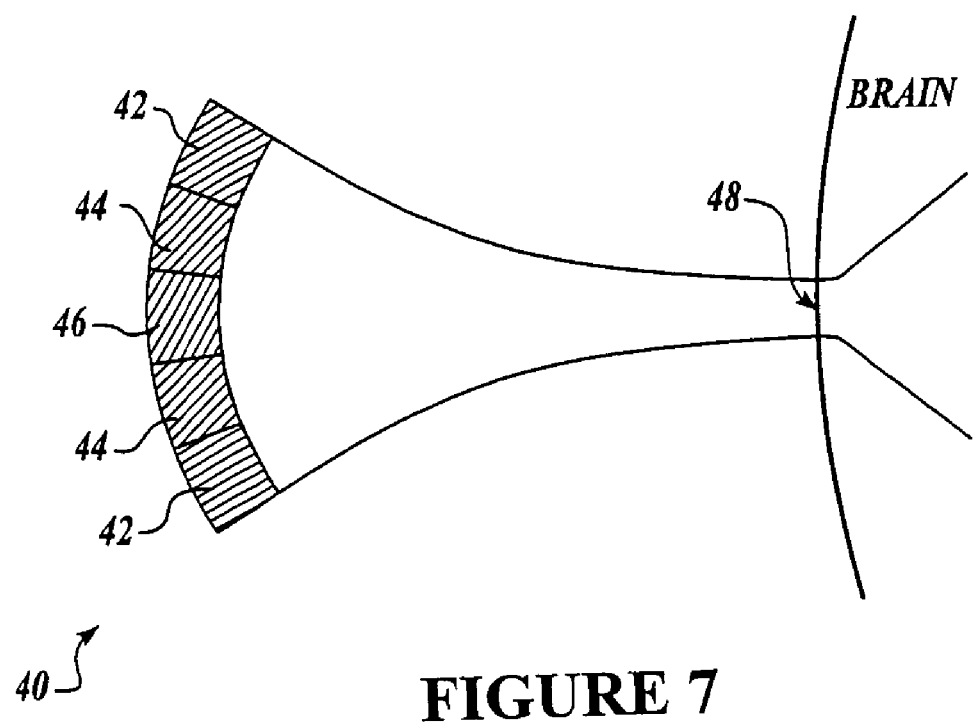
FIG. 7 is a schematic diagram illustrating another system of the present invention for inducing and detecting tissue deformation for assessing cardiac tissue properties.

FIG. 7 illustrates one embodiment of an acoustic source and probe combination 40 that is especially suitable for use with the active mode of tissue assessment of the present invention. Source and probe combination 40 comprises confocal, annular acoustic sources 42 and 44 and a diagnostic ultrasound probe 46. Phasing acoustic sources 42 and 44 at slightly different frequencies produces a significant radiation force only at their mutual focus, indicated in the cardiac tissue, such as near the ventricular wall surface, schematically illustrated at location 48, and deforms the tissue. When a single acoustic source is used, or the sources are used such that there is no difference in frequency between the sources, the result is a unidirectional displacement of the target tissue that coincides with their overlapping foci, with negligible oscillatory component for the duration of each acoustic pulse. Under these circumstances, repeated single-frequency pulses will create periodic pulsations of the tissue at the frequency of the PRF. In either embodiment, acoustic emissions may be generated from the transiently deformed tissue, with the emissions monitored by transducer 46 and related to tissue properties or physiological conditions.

The acoustic source and probe combination 40 illustrated in FIG. 7 may also be used, in combination with an imaging system, to acoustically palpate tissue at target sites to localize tissue responses to the focused ultrasound. The imaging system may employ ultrasound or another tissue imaging modality, such as magnetic resonance imaging, computed tomography, fluoroscopy, or the like. Using an acoustic source and probe combination having ultrasound imaging capability, for example, provides visualization of the target site and aids targeting of the acoustic radiation force and localization of responses.

Figure 8:
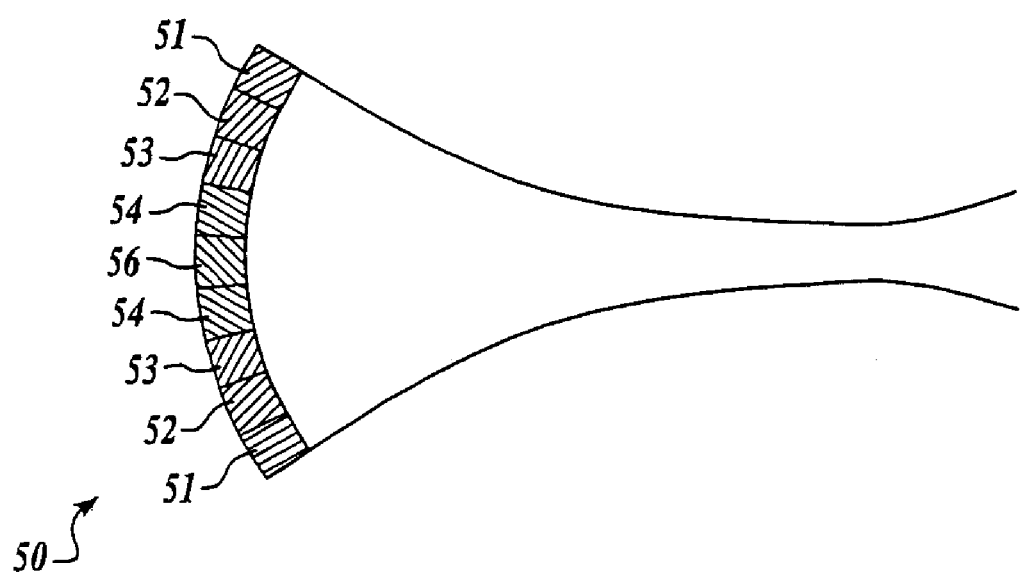
FIG. 8 is a schematic cross-sectional diagram illustrating the use of confocal acoustic sources to produce tissue displacement and a diagnostic ultrasound probe to measure the amplitude of the displacement.

FIG. 8 illustrates another acoustic source and probe combination 50 comprising a plurality of ultrasonic transducers 51, 52, 53 and 54, arranged as concentric annular elements. Each annular acoustic source represents a single frequency source of ultrasound that cooperates, with the other acoustic sources, to interrogate and/or displace tissue at a selected location. The foci of the annular transducers is the focus of the interrogation signal, or the radiation force, and the location of assessment of intrinsic tissue displacement and/or induced tissue displacement and/or emissions. More or fewer ultrasonic transducers may be used. A larger number of annular transducers generally provide a greater degree of control and precision of where the interrogation signals, or the radiation force, is focused. This arrangement of annular transducers may also be used, in a variable frequency mode, to generate an oscillatory radiation force in target tissue. When multiple acoustic sources are used, each source is operated by a controller, amplifier and function generator, but operation of the separate acoustic sources is controllable using a centralized control system. This acoustic system may be further generalized or modified for specific applications by using a non-annular or non-axial distribution of transducers to allow for additional ultrasound beam forming or electronic steering.

Detection element 56 is provided in acoustic combination 50 to detect at least one aspect of intrinsic and/or induced tissue displacement. In one embodiment, element 56 comprises a diagnostic ultrasonic probe that emits an ultrasonic pulse toward the site of tissue displacement and detects its echo to track the magnitude, or other aspects, of tissue displacement. In another embodiment, element 56 comprises an ultrasound probe, such as a transcranial Doppler, that detects the Doppler shift produced by the tissue displacement. In yet another embodiment, detection element 56 comprises a hydrophone that detects the sound waves emitted by tissue in which an acoustic radiation force is generated.

Commercially available components may be used in systems of the present invention. The following description of specific components is exemplary, and the systems of the present invention are in no way limited to these components. High intensity focused ultrasound transducers are available from Sonic Concepts, Woodinville, Wash. Multi-element transducers have been used by researchers and are described in the literature. A multiple focused probe approach for high intensity focused ultrasound-based surgery is described, for example, in Chauhan S, et al., Ultrasonics 2001 Jan, 39(1): 33–44. Multi-element transducers having a plurality of annular elements arranged, for example, co-axially, are suitable. Such systems may be constructed by commercial providers, such as Sonic Concepts, Woodinville, Wash., using technology that is commercially available. Amplifiers, such as the ENI Model A150, are suitable and are commercially available. Diplexers, such as the Model REX-6 from Ritec, are suitable and are commercially available. Function generators, such as the Model 33120A from HP, are suitable and are commercially available. Many types of controllers are suitable and are commercially available. In one configuration, a Dell Dimension XPS PC incorporates a Gage model CS8500 A/D converter for data acquisition, and utilizes LabView software from National Standards for data acquisition and equipment control. In some embodiments, an ATL transcranial Doppler probe, Model D2TC, is used for detection.

One aspect of the present invention relates to acoustic source/detector systems for use in methods and systems of the present invention. In operation, an acoustic source/detector combination, such as a TCD transducer/detector, is stably mounted, or held, in proximity to a surface in proximity to an acoustic window, such that the focus of the acoustic source(s) is adjustable to provide an acoustic focal point within, or on, or in proximity to, myocardial tissue. The acoustic source/detector combination is preferably provided as a unitary component, but separate components may also be used. The acoustic source/detector combination may be mounted on a stabilizer, or in a structure, on the chest. An applicator containing an acoustically transmissive material, such as a gel, may be placed between the surface of the acoustic source/detector combination and the chest. An acoustic source/probe combination may be provided in a holder that is steerable to facilitate probing of various targeted tissue sites within a general situs. Steering of the acoustic device may be accomplished manually or using automated mechanisms, such as electronic steering mechanisms. Such mechanisms are well known in the art.

In one embodiment, one or more transducer array(s) are used for acquisition of acoustic data, and data is processed using accompanying processing, storage and control functions. In general, such transducer arrays may be referred to as "phased arrays," since the individual acoustic elements within the array are coordinated with one another. Transducer arrays may be used in either or both passive and active modes of operation, and may be used in imaging modes to display data relating to cardiac tissue properties and cardiac parameters. Many imaging and display techniques are known in the art and may be used to highlight various types and aspects of acquired data.

In one embodiment, one or more transducer arrays may be operated simultaneously, or alternately, in active and passive modes of operation. Using a programmable acoustic transducer array, for example, multiple tissue sites may be acoustically interrogated in an active or passive mode simultaneously, or intermittently at pre-selected time intervals. Similarly, acoustic scatter data may be collected from multiple target cardiac tissue sites simultaneously, or intermittently. In one embodiment, for example, tissue properties of target myocardial tissue may be determined based on acquired acoustic data while mean and/or continuous ABP is determined simultaneously based on acoustic data acquired from or in proximity to blood vessel(s).

Figure 9:
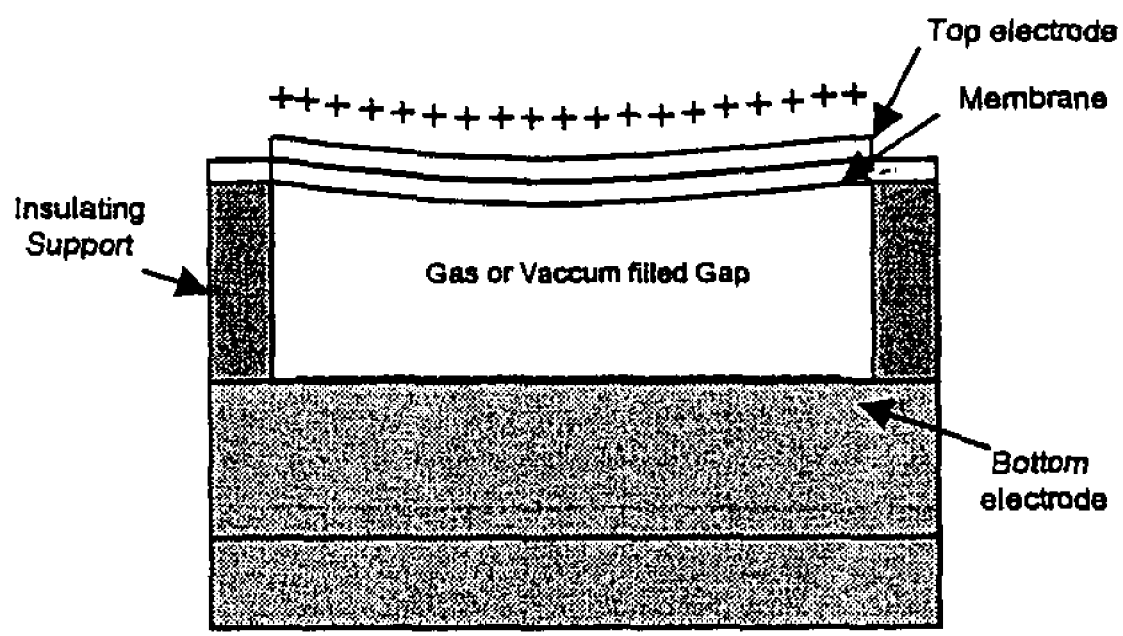
FIG. 9 shows a schematic illustration of a single cMUT array transducer cell structure.

In one embodiment, acoustic arrays of the present invention comprise capacitive micromachined ultrasound transducers (cMUT). cMUT transducer arrays may be used in both active and passive modes of operation according to the present invention. cMUT ultrasonic transducers are manufactured using semiconductor processing techniques and have sufficient power and sensitivity to transmit and receive at diagnostic ultrasound energy levels, which is necessary and sufficient for our purposes. The transducers are made by fabricating very small capacitive diaphragm structures in a silicon substrate. FIG. 9 shows a single cMUT array transducer cell structure. These diaphragm-structures convert acoustic vibrations into a modulated capacitance signal or vice versa. A DC bias voltage is applied and an AC signal is either imposed on the DC signal in transmission or measured in reception. A cMUT array is composed of multiple individual cell structures arrayed in rows and/or columns.

In one embodiment, two cMUT acoustic arrays are aligned in a sparse two-dimensional (2D) array known as a "Mills Cross" configuration, which allows one array to sweep vertically in send and receive modes and the other to sweep horizontally in receive and send modes. In this implementation, two crossed linear cMUT arrays alternatively transmit and receive ultrasound while electronically steering the sending and listening beams, to identify and focus on the acoustic signal that has the largest Doppler shift using, for example, range-dependent Doppler methodologies described below. In alternative embodiments, the send and receive modes of the acoustic arrays may be reversed, or a single array may be used to both send and receive acoustic signals. Full 2D transducer arrays having acoustic elements arranged in any two-dimensional configuration may also be used. Three dimensional transducer arrays may also be used with appropriate control and processing systems. In yet another embodiment, a cMUT array may be used in combination with a PZT transducer, with the PZT transducer serving as the acoustic source and transmitting around the cMUT array, and the cMUT array serving as the acoustic detector.

cMUT transducer arrays have the potential of being produced very inexpensively, and may also have the support electronics integrated onto the same chip. In one embodiment, acoustic arrays of the present invention are provided as a disposable component of an ICP monitoring device comprising one or more transducer arrays in operative communication with a data processing, storage and display device. The one or more transducer arrays may communicate with a data processing, storage and display device by means of one or more cables, or using a radio frequency or other wireless technology. The transducer array(s) may be steerable and may be programmed to scan, identify one or more desired target site(s), and maintain focus on that target site in an automated fashion. Transducer arrays of the present invention may also be programmed to collect acoustic data from multiple target sites simultaneously, or at different times. In one embodiment, a transducer array, or a plurality of arrays, may be programmed to operate alternatively as acoustic sources and detectors. In one embodiment, multiple transducer arrays used for monitoring multiple patients provide data to and communicate with a single data processing, storage and display device.

In another embodiment, an acoustic array comprising PVDF (polyvinylidene fluoride) film transducers is used as an acoustic detector array, in combination with a cMUT array or a single element PZT transducer employed as the source. In this embodiment, the source transducer or array transmits sound through the PVDF array, sweeping the sound in a single dimension generally perpendicular to the arrangement of the PVDF array. The PVDF array serves as the acoustic detector, receiving and processing acoustic signals. An acoustic array of the present invention may comprise a combination of PVDF and cMUT arrays. The combined depth of the arrays may be on the order of 1 cm. The cMUT array is arranged below the PVDF array and transmits sound through the PVDF array. The PVDF array may be made in two dimensions, so that it can detect acoustic signals in two directions, rather than the single direction illustrated.

Alternatively, an acoustic array of the present invention may comprise a combination of a PVDF array and one or more PZT transducer(s). The PVT transducer may be mounted below the PVDF array and transmit through the PVDF array in a single, broad beam. The PVDF array may be constructed as a single dimension array, or as a two dimensional array. An acoustic array having a two dimensional PVDF array has the capability of receiving acoustic signals in two dimensions and an underlying PZT transducer. This system may alternatively employ a cMUT array in the place of the PZT transducer.

Systems of the present invention may comprise both non-disposable and disposable or reusable components. Costly elements of the acoustic system are provided as non-disposable components, while less costly components, which require close interaction with a patient and, perhaps, sterilization, are provided as disposable components.

In one embodiment, an acoustic array is provided as part of a disposable system element, in combination with a patient interface component. The acoustic array is preferably in contact with acoustically transmissive material, such as an acoustic gel, that provides high fidelity acoustic transmission into and from the target area. The acoustically transmissive material is preferably interfaced with a contact material, such as an adhesive material, that facilitates temporary positioning and affixation of the disposable system element to a patient's skin. The patient contact material may be protected by a removable cover, which is removable at the time of use. The disposable system element, including the acoustic array, may be provided as a unitary element that may be sterilized and packaged for one-time use.

Alternative disposable systems and elements may also be employed. In one such alternative system, acoustically transmissive material layers may be provided as a separately sterilized, packaged component that is designed to interface with a non-disposable component including the acoustic array(s). Such layers may be provided with an adhesive layer on one side for contact with the patient's skin. Or, a recess may be provided for manual application of acoustically transmissive material. It will be evident that many different embodiments and arrangements of disposable and non-disposable elements may be employed.

This compact, disposable array element may be placed in contact with the skin of a patient at an acoustic window and, when activated, electronically focuses the acoustic source(s) and detector(s) on the target site of interest, such as a target myocardial tissue site. The acoustic array monitors and stays focused on the target area of interest during operation. In this embodiment, the acoustic array forms part of a disposable assembly including an acoustic gel, or another acoustic material that facilitates transmission of acoustic signals at the interface with the patient's skin during operation. The exposed surface of the acoustic gel is preferably interfaced with one or more adhesive elements that facilitate temporary placement on and consistent contact with a desired patient surface. A removable cover may be provided over the acoustic gel to preserve the acoustic array and other components. These elements may be provided as a disposable unit that is mountable on non-disposable elements of the system. Non-disposable elements of the system may include mounting hardware, one or more cables or wireless transmission interfaces, and a data processing, storage and display device.

Placement of the acoustic source(s) and detector(s) on a subject for assessment of acoustic properties of myocardial tissue (including blood and blood vessels) may be at known "acoustic windows." The placement of the source(s) with respect to the detector(s) will depend on the acoustic data desired—e.g., for collection of back scatter acoustic data, the source(s) and detector(s) are in proximity to one another, while the source(s) and detector(s) are positioned generally opposite one another for collection of forward scatter acoustic data. Acoustic scatter or reflection data may be collected at various angles by placing the source(s) and detector(s) at various locations on the patient.

To ensure that representative target tissue is sampled, the target tissue location must be volumetrically large enough to provide a representative sample. The volumetric sampling requirements will vary, of course, according to tissue type and location. In general, target sites having tissue volumes of from 1 $mm^3$ to about 100 $cm^3$ are suitable, and target tissue sites having tissue volumes of less than about 5 $cm^3$ are preferred. Acoustic data acquisition techniques of the present invention may be used in combination with known ultrasound imaging techniques to provide visualization of the target tissue sites.

Data, such as acoustic scatter data, relating to intrinsic and/or induced tissue displacements is processed according to methods and systems of the present invention and related to medically relevant physiological properties, such as cardiac output and other cardiac parameters. Exemplary data processing techniques for making various correlations based on various types of acquired data are well known. Although these data processing techniques are based on the acquisition of acoustic scatter data, they may be applied, as well, with modifications that would be well known in the art, in other modalities, such as near infrared spectroscopic (NIRS) modalities and magnetic resonance modalities.

For some applications, as mentioned previously, relative trend determinations of cardiac tissue properties over time, or at different points within or over multiple cardiac cycles, are useful. In other applications, it is useful to compare measured, or determined values for cardiac tissue properties to standard values based, for example, on empirical data. In this way, abnormal, or dysfunctional tissue may be identified by comparison to "normal" or "functional" tissue values.

In one embodiment, a small specialized ultrasonic palpation device is placed on the subject's chest and aimed, through the ribs, to a target cardiac tissue site at or near the right ventricular wall. This may be achieved using a diagnostic ultrasound scan head placed confocally with the palpation device, so that the focus of the palpation device is registered on the screen and visible to the person implementing this procedure. In another embodiment, a simple A-mode transducer/hydrophone is used to aim, palpate and display data, and provides a stand-alone device. The right ventricle is exemplary, but, in practice, this technique may be used to with focus ultrasound beams to targeted site at or near cardiac tissue. This combined palpation and aiming scan head is preferably secured to the outside of the chest for the duration of the medical procedure, with the assessment being initiated when the patient's blood volume and cardiac volume are normal.

With the specialized palpation device properly aimed, one can, in one embodiment, apply a constant-amplitude oscillatory radiation force to the right ventricular wall, which causes that focal portion of tissue and a rim of adjacent tissue to oscillate. This may be done by the application of focused ultrasound with a dual-annular array, with each annulus operating at slightly different frequencies from one another. The frequency of the oscillatory radiation force will be that of the difference frequency of the two annuli. For a given tension in the right ventricular wall, i.e., at a given part of the cardiac cycle, and for a given constant amplitude forcing, there will be a difference frequency, hence oscillation rate, in the radiation force that maximizes the acoustic emissions from the point of application of the radiation force. This frequency may be referred to as the resonant frequency of the ventricle wall. As the wall tension changes for a variety of reasons, this resonant frequency will change: the greater the tension the higher the resonant frequency, while the lower the tension the lower the resonant frequency.

Commercially available hydrophones may easily be integrated into the ultrasonic palpation device for tracking the acoustic signals emitted from the target cardiac tissue. By tracking this resonant frequency, starting with a baseline determined while the patient is awake, preoperatively or newly anesthetized but before a change in blood volume, one can, with concomitant blood pressure measurements, assay where the patient is on the Starling curve. For example, if the resonant frequency dips significantly lower than the patient-specific average normal value, this would be consistent with the ventricle walls becoming more flaccid. If this were to occur while blood pressure drops, then these observations would be strong evidence of hypovolemia. If the resonant frequency becomes significantly higher than the patient-specific average normal value, this would be consistent with the ventricle walls becoming stiffer. If this were to occur while blood pressure drops, then these observations would be strong evidence of hypervolemia. One could continue tracking cardiac wall stiffness in this fashion throughout the medical procedure of interest, until the patient is safely stabilized.

In an alternative embodiment that is otherwise similar to the embodiment described above, one could use more than two annuli in the array. And, in another alternative embodiment that is similar to that described in the previous paragraph, one could use a single or multi-element array operated in a continuous wave (CW) mode, and vary the amplitude of the applied signal at a frequency that would induce the desired oscillations in the tissue. And, in yet another alternative embodiment that is similar to that described in the previous paragraph, one could use a single or multi-element array operated in a pulsed mode, and vary the pulse repetition frequency of the applied signal until the resulting temporal series of pulses induces the desired oscillations in the tissue. There are costs and benefits associated with each choice of palpation device.

In another embodiment, we apply a constant-amplitude oscillatory radiation force, using one of the several methods described above. Rather than search for a resonant frequency, however, we work with a given frequency that from experience is known to be above or below the resonant frequency of the heart's right ventricle wall. We then track the amplitude of the palpation-induced acoustic emission from the heart, both within a cardiac cycle and over many cardiac cycles, starting while the patient's cardiac volume is normal, and then proceeding throughout the medical procedure of interest until the patient is safely stabilized. For example, consider the case where one was driving the local heart tissue into an oscillation whose frequency was always below the resonant frequency of the local heart tissue. If the average amplitude of the ultrasound-induced acoustic emission were observed to increase over time, this would be consistent with a reduction in the resonant frequency of the heart tissue, approaching the driving frequency of the acoustic radiation force from above. This would suggest that the ventricle walls were becoming more flaccid than on average. This observation, in conjunction with an observed drop in blood pressure, would give strong evidence of hypovolemia. If, under the same assumptions, the average amplitude of the ultrasound-induced acoustic emission were observed to decrease over time, this would be consistent with an increase in the resonant frequency of the heart tissue, moving up and away from the driving frequency of the acoustic radiation force. This would suggest that the ventricle walls were becoming stiffer than on average. This observation, in conjunction with an observed drop in blood pressure, would give strong evidence of hypervolemia.

In another embodiment, any one of several aspects of safe, ultrasound-induced deformation of the right ventricular wall of the heart is assayed, using, for example, an A-mode transducer placed confocally with the ultrasound palpation device. As described above, the palpation device may have one of several manifestations. Also, one would likely not need the absolute value of the deformations, just the trend in those deformations over time, as well as concomitant measurements of blood pressure, starting when the patient's cardiac volume is normal, and ending when the patient is safely stabilized.

According to yet another embodiment, cardiac tissue is not "palpated" at all. Instead, the local strain within a small portion of the cardiac ventricle wall tissue is tracked using, for example, an A-mode ultrasound system, optionally in conjunction with standard diagnostic ultrasound image. The local strain is assayed using sonoelasticity analysis on the resulting acoustic backscatter signal, a well-known technique developed over the last 15 years and often applied for assaying the presence of breast cancer. Sonoelasticity analysis would give a measure of the scale of the intrinsic deformations of tissue, essentially the average change in spacing of two close points within the tissue (distances of millimeters or less) divided by their average spacing at systole or diastole, for example. By tracking such intrinsic deformations within or near the same place in the ventricle, the stiffness of the ventricle walls is monitored, which relates to cardiac output, as discussed above. For example, for a fall in blood pressure and cardiac output, as the stiffness of the heart tissue decreased, the intrinsic displacements of portions of the ventricle wall would increase, thereby suggesting hypovolemia. As the ventricle walls increased in stiffness, the intrinsic displacements of portions of the ventricle wall would decrease, thereby suggesting hypervolemia. In an alternative embodiment, or one that might be of use as a complement to the sonoelastic measurement scheme described above, one could gain useful information by tracking through time the macroscopic displacement of the heart tissue in one place in the heart, on the scale of a centimeter or so. Large macroscopic displacements of a fixed portion of heart tissue with low blood pressure would suggest low cardiac output due to hypovolemia, while small macroscopic displacements of heart tissue—likely after a large net displacement away from the center of mass of the heart, towards the transducer—coupled with low blood pressure, would be consistent with low cardiac output due to hypervolemia.

Arterial Blood Pressure Using "Passive" or "Active" Mode

In another aspect of methods and systems of the present invention, intrinsic and/or induced changes in the diameter or other geometric properties of a blood vessel, or changes in the intrinsic or induced displacement in tissue surrounding blood vessels, are monitored and assessed using ultrasound, and this information is related to synchronous Doppler flow measurements within the same vessel. In an active mode, tissue displacement may be induced in a blood vessel or in tissue surrounding a blood vessel by application of an acoustic radiation force, as described above. Similarly, in a passive mode, intrinsic tissue displacements at or near a blood vessel may be detected using a variety of techniques, with the use of ultrasound techniques being preferred. In some embodiments, an initial assessment is performed, using Doppler flow measurements or ultrasound detection techniques, to locate a desired blood vessel and thereby provide a focus for identifying intrinsic and/or induced displacements at or near the vessel.

Since the diameter (or other geometric properties) of the vessel is a function of the pressure being exerted against the wall of the vessel by blood, and since the velocity of blood flow is dependent on the diameter (or radius) of the vessel through which the blood travels, blood pressure can be calculated from flow velocity measured by Doppler. Geometric properties of vessels that may be evaluated using methods and systems of the present invention include changes in diameter, cross-sectional area, aspect ratio, rate of change of diameter, velocity, and related parameters. By simultaneously measuring the pulsatility of the blood vessel of interest and the Doppler flow velocity proximal and distal to this site, continuous blood pressure is determined. Specific methods for assessing ABP are described below.

Blood pressure may also be assessed, in an active or passive mode, by examining acoustic properties of target tissue sites at or in proximity to blood vessels. The acoustic properties of target tissue at or in proximity to blood vessels can be related to tissue stiffness or compliance, which can be related to blood pressure.

Blood pressure measurements made using the passive or active acoustic modes described herein may also be used for calibration of existing invasive or non-invasive blood pressure monitoring devices. Thus, the methodology described below, particularly with reference to blood pressure determinations using the active acoustic mode, may used in combination with existing blood pressure monitoring devices, which are available, for example, from Medwave Corporation, St. Paul, Minn.

Correlation of Non-Invasively Measured Spontaneous Vessel Wall Displacement With Doppler Flow and ABP This method uses a derived relationship between spontaneous vessel wall displacement (due to blood pressure and smooth muscle tonal responses to the hemodynamic state), synchronous velocity of blood flow within the vessel of interest, and invasively monitored ABP to estimate ABP from non-invasively measured vessel wall displacement and Doppler flow velocity. Using an ultrasound probe, the given vessel of interest is insonated with a waveform of specific frequency and amplitude, and the time or phase shift of a particular reflected or backscattered or echo signal is used to calculate spontaneous tissue displacement.

The equation that relates time or phase shift to tissue displacement is $d = t*1500$ m/sec, where d=tissue displacement, t=the time or phase shift of the reflected signal, and 1500 m/sec is the estimated speed of sound through tissue. The relationship between d, synchronously measured Doppler flow velocity within the vessel of interest (i), and invasively measured ABP is then determined by taking simultaneous measurements of spontaneous vessel wall displacement, flow velocity, and ABP and solving for the equation: $ABP = F(d, i)$, where F can be any function, such as an exponential, vector, matrix, integral, etc., or a simply an empirical relationship. Once F is established (by means of multiple empirical measurements from a variety of patients under various circumstances), the non-invasive determination of vessel wall displacement and flow velocity is used to calculate ABP. A calibration step using, for example, a cuff plethysmograph to measure ABF, may be implemented before continuous, noninvasive ABP measurements are made.

Correlation of ABP with Amplitude of Vessel Wall Signal and Doppler Flow Velocity This method uses a derived relationship between the amplitude of the reflected vessel wall signal, Doppler flow velocity, and invasively monitored ABP to estimate ABP from non-invasively measured vessel wall signal and Doppler flow velocity (i). Using an ultrasound probe, a particular vessel of interest is insonated with a waveform of specific frequency and amplitude, and the amplitude of the backscatter is used to create a waveform of vessel wall reflection/absorption. This new waveform, a, is generated by integrating the amplitude of the backscatter over a finite epoch (such as the cardiac cycle, measured with ECG tracing) and normalizing this by the time period of the epoch. The relationship between this derived waveform, a, and invasively measured ABP is then determined by taking simultaneous measurements of the backscatter signal, Doppler flow velocity, and ABP and solving for the equation: $ICP = F(a, i)$, where F can be any mathematical function, or simply an empirical relationship. Once F is established (by means of multiple empirical measurements from a variety of patients under various circumstances), the non-invasive determination of a can be used to calculate ABP. A calibration step using a cuff plethysmograph to measure ABP may be implemented before continuous, noninvasive ABP measurements are made.

Correlation Between Peak Backscatter Amplitude and ABP

In a manner similar to that described above, the peak amplitude of the backscatter signal over a given epoch (e.g., cardiac cycle) is normalized by the baseline value of the backscatter signal over the same epoch, and this, along with Doppler flow velocity, is related to the simultaneous invasive measurements of ABP. A calibration step using a cuff plethysmograph to measure ABP may be implemented before continuous, noninvasive ABP measurements can be made.

Methods and systems of the present invention may be used in a variety of settings, including emergency medicine settings such as ambulances, emergency rooms, intensive care units, and the like, surgical settings, in-patient and out-patient care settings, residences, airplanes, trains, ships, public places, and the like. The techniques used are noninvasive and do not irreversibly damage the target tissue. They may thus be used as frequently as required without producing undesired side effects. The methods and systems of the present invention do not require patient participation, and patients that are incapacitated may also take advantage of these systems. The methods and systems of the present invention for assessing cardiac tissue may be used on a continuous or intermittent basis.

EXAMPLE 1

Figure 10A:
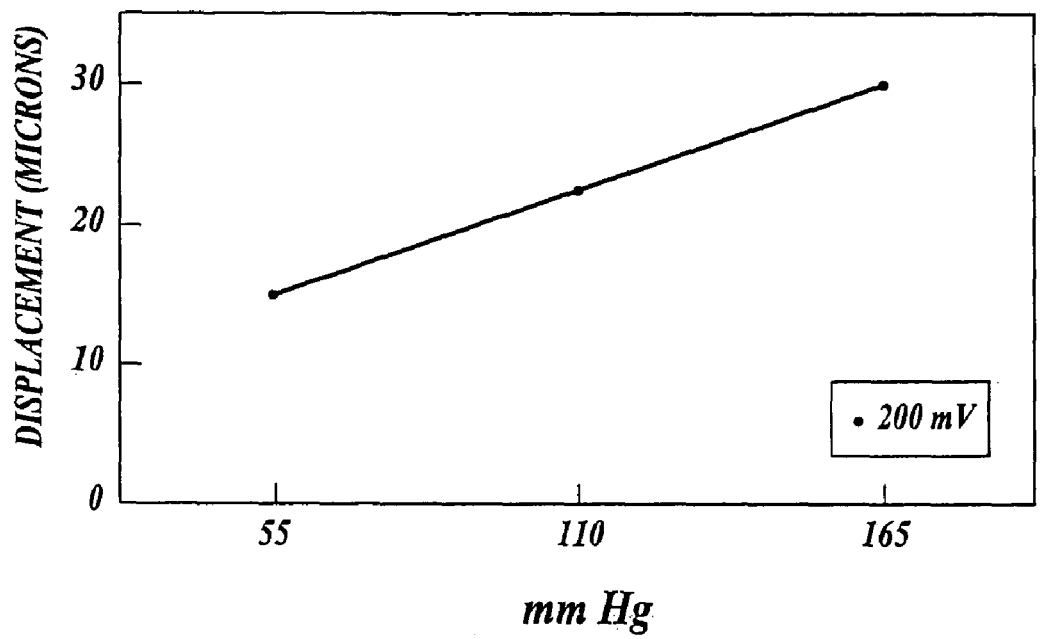
FIG. 10A shows a plot demonstrating measured displacement of in vitro beef brain as a function of increasing simulated ICP and as a consequence to increasing brain CSF volume.

Brain tissue was used as a model experimental system. We have shown in vitro (FIG. 10A) and in vivo (FIGS. 10B-D) and describe in detail below, that intrinsic displacements of brain tissue (e.g. compressions and distensions), and their various acoustic scatter properties, can be directly measured using a standard transcranial Doppler (TCD) transducer, off-the-shelf data acquisition systems, and novel analysis of the acoustic backscatter signal from brain. Myocardial tissue displacement may be measured in the same fashion and related to tissue strain, tension, and the like, as described above, to make noninvasive assessment of cardiac tissue and parameters.

An in vitro model for examining changes in ICP using acoustic techniques was constructed using fresh bovine brain immersed in fluid in a water-tight, visually and acoustically transparent bottle attached to a hand-pump for changing the pressure on the brain. An acoustic transducer (ATL/ Philips Medical Systems, Bothell, Wash.), and the bottle, were placed in water so that the focus of the interrogation transducer was near the edge of the brain, but within the brain. Using a transducer whose amplifier was driven at 200 mV and a LeCroy Waverunner oscilliscope, we collected acoustic waveforms backscattered from the brain generated by the interrogator that showed, measured by changes in arrival times, that increases in displacement of beef brain as a function of increased pressure on the in vitro beef brain, as determined by a gauge on the hand pump, were linearly related (See FIG. 10A). This was the expected result: as the pressure on the brain (ICP) increases as a consequence of increasing liquid (CSF) volume in a confined space, we would expect to see the brain move away from the container.

Figure 10B:
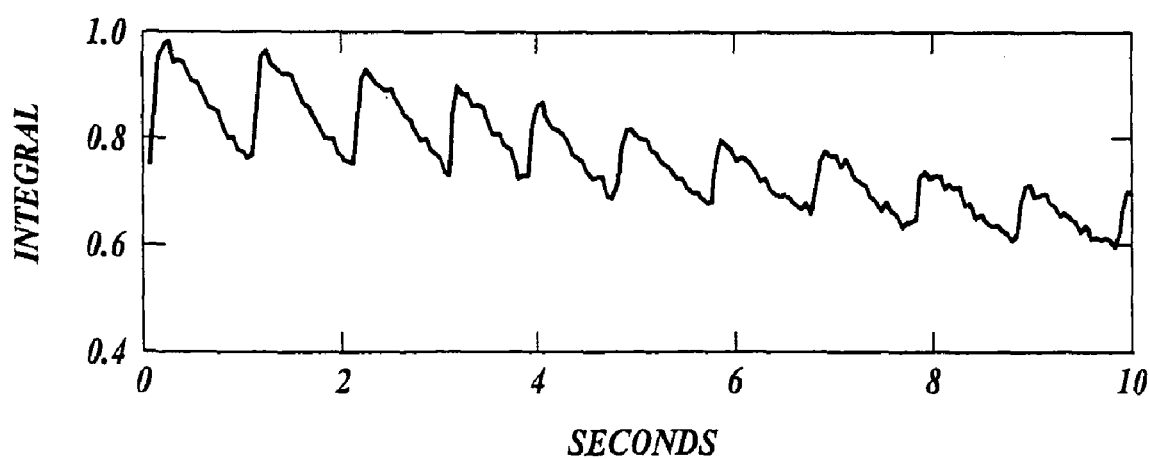
FIG. 10B shows a backscatter trace of human brain, in vivo, while the subject was holding his breath.
Figure 10C:
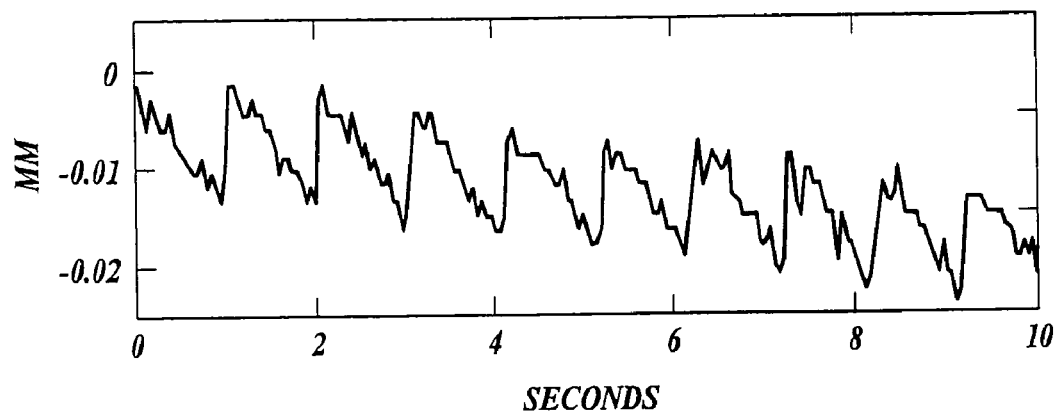
FIG. 10C shows the displacement of human brain, in vivo, while the subject was holding his breath.
Figure 10D:
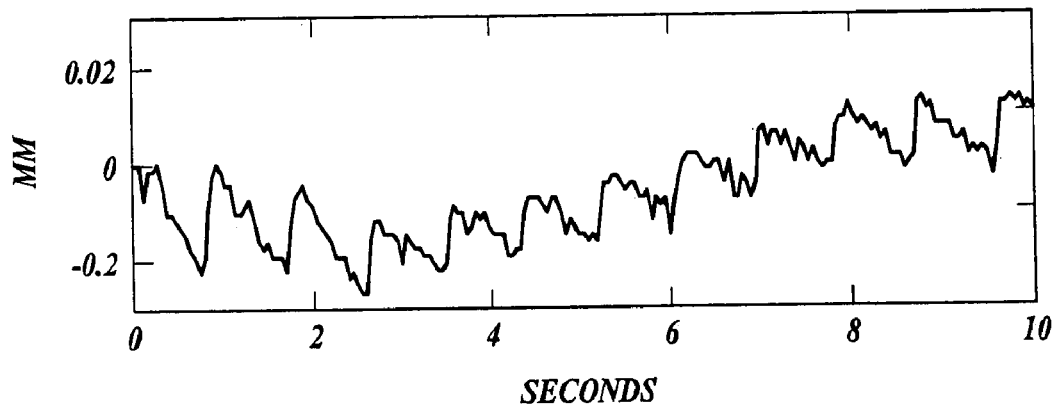
FIG. 10D shows the displacement of human brain, in vivo, while the subject first held his breath and then inhaled.

The displacement (compression and distension) waveforms shown in FIGS. 10B-D were produced using ultrasound techniques to measure acoustic scatter signals associated with intrinsic displacements of human brain tissue in situ. An acoustic transducer (ATL/Philips Medical System, Bothell, Wash.) was used to insonate target CNS tissue with acoustic interrogation signals having $10$–$10^3$ acoustic pulses per second at 2.25 MHz containing 3–15 cycles of ultrasound with peak negative pressures less than 2 MPa or 20 bar. Using a LeCroy Waverunner oscilliscope, we collected acoustic waveforms backscattered from the brain generated by the interrogator and calculated the tissue displacement.

This calculation was made using a normalized correlation of paired received signals. Given an estimate of the speed of sound in brain and the calculated temporal displacement, the spatial displacement of the tissue at a given moment may be calculated. Tracking the spatial displacement over time provides a direct measure of the displacement of the brain tissue that is being noninvasively interrogated by the diagnostic ultrasound. This calculation can also be made by correlating the backscattered signal with a reference interrogation signal, noting when the interrogation signal is sent and when the backscattered signal is received. Changes in the amplitude of the backscatter from the region of interest may also be monitored to determine the ICP waveform. For example, we have found that by integrating the acoustic backscatter signal over a short time interval of about 5 to 10 ms at the region of interest, and normalizing that integral by the length of that time interval, we developed a time series that has the salient features of a typical ICP waveform. In particular, for small volumes of measured brain displacement, the signal derived from following displacements or from following the normalized integral of the backscatter looks identical to the time course of the mean velocity of blood in the middle cerebral artery of the test subject.

FIGS. 10B-D show changes in properties of a human brain over time, measured in situ, using ultrasound techniques according to the present invention, as described above. Certain physiological behaviors, such as holding breath, sneezing, etc., are known to transiently increase or decrease ICP.

FIG. 10B shows changes in the normalized amplitude of the acoustic backscatter as the human subject held his breath. FIG. 10C shows the displacement of human brain as the human, based on correlation techniques, while the subject was holding his breath, using pulses with 15 cycles of ultrasound. In particular, FIG. 10C shows the net increased displacement of brain towards the transducer as the pressure on the brain increased due to an accumulation of blood volume in the brain, along with the cardiac-induced brain displacement signals.

FIG. 10B shows the same kind of received signal characteristics as FIG. 10C, where we used pulses with 5 cycles, but analyzed the data by integrating over the acoustic backscatter signal as described above. As in FIG. 10C, both waveforms changed over the 10 seconds while the subject held his breath, consistent with known transient changes in ICP when subjects hold their breath. The vascular pulse and autoregulation waveforms are present, in modified form, in FIG. 10C. The time series of FIGS. 10B and 10C look similar to the velocity pattern found in the patient's middle cerebral artery (data not shown). This measurement is therefore an accurate representation of the compression and distension of brain parenchyma in response to the major cerebral arteries, supplemented by contributions from the rest of the cerebral vasculature.

FIG. 10D shows an example of changes in near-surface brain displacement as the subject first held his breath for 2–3 seconds, then inhaled. Changes in respiration and the respiratory cycle are known to transiently change ICP. At first, the brain surface's net displacement toward the transducer increased. Upon inhalation, the brain tissue moved, over several cardiac cycles, away from the transducer. The observed displacement is consistent with the transient changes in ICP expected when a subject holds his breath (transient blood volume and ICP increase) and then inhales (transient blood volume and ICP decrease).

Our measurements were made over a small volume of brain tissue (of order 1.0 cm$^3$). We anticipate that measurements of brain tissue displacement (e.g. compression and distension) of a relatively large volume of brain tissue (on the of order 10 cm$^3$) will produce a signal that looks identical to a typical ICP trace. This signal is used directly, or with ABP data, to assess ICP and/or autoregulation status, as discussed above. Contributions to the acoustic backscatter signal over a large volume of brain tissue are the result of the average displacements (distension and compression) of brain tissue produced by a plurality of cerebral blood vessels, whose particular intrinsic oscillations will cancel, except for the major ones (dicrotic notch, etc), which will reinforce one another, as observed invasively.

EXAMPLE 2

We have shown, in vitro, using a beef brain model similar to that described above, that a palpation pulse of ultrasound across a range of acoustic intensities can cause increasing displacements of brain without causing gross tissue damage. Palpation of myocardial tissue using ultrasound pulses may be achieved in a similar fashion.

Fresh bovine brain was immersed in fluid in a water-tight, visually and acoustically transparent bottle attached to a hand-pump for changing the pressure on the brain. ATL acoustic transducers (ATL-Philips Medical Systems, Bothell, Wash.), and the bottle, were placed in water so that the focus of the acoustic palpation and interrogation transducers were near the edge of the brain, but within the brain. Using LeCroy Waverunner oscilloscope, we collected acoustic interrogation waveforms backscattered from brain. For palpating and interrogating beef brain, in vitro, the interrogation pulses were administered as described with respect to FIG. 10A, while the palpation pulses had a pulse repetition frequency of 1 Hz, contained 30,000–50,000 cycles, and had a time-averaged intensity of less than 500W/cm$^2$.

Figure 11:
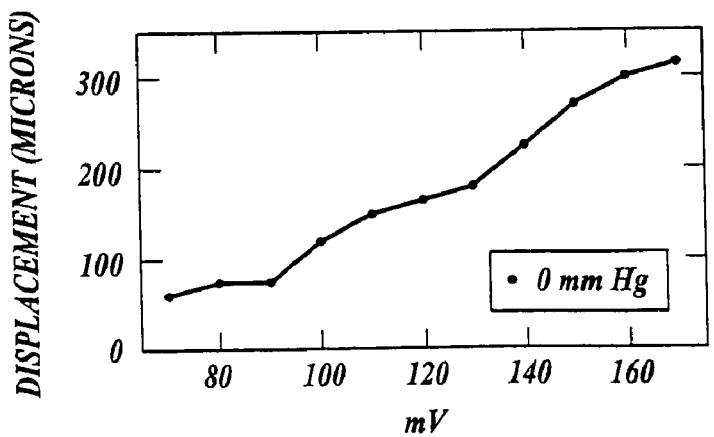
FIG. 11 illustrates experimental results showing that the measured displacement of brain tissue, in vivo, is proportional to the acoustic radiation force applied, as indicated by the acoustic driving voltage.

As shown in FIG. 11, as the acoustic force of the ultrasound increases (proportional to the driving voltage given in mV) at ambient (0 mmHg) pressure, so does the measured displacement of the beef brain, given in microns. We have also shown in the experimental beef brain model described above, in vitro, that brain displacement due to identical ultrasonic palpation pulses decreases from 300 μm to 210 μm as the pressure on the brain increases from 0 to 55 mm Hg. Therefore, when the same acoustic force is applied with ultrasound, brain-tissue displacement in vitro is inversely proportional to ICP, as expected. Noninvasive, ultrasound-based measurements of ultrasonic palpation of brain tissue can be safely used to directly measure ICP in humans, without the need for blood pressure measurements, because by this method the brain will be subjected to a known (ultrasonic) force. Alternatively, using a focused ultrasound beam with an intensity less than a value easily determined to be safe, probing or palpation of brain tissue with a known force will also yield data ancillary to the passive method of ICP determination, by calibrating the amount of deformation brain tissue undergoes when subjected to a known compressive force.

All of the publications described herein, including patents and non-patent publications, are hereby incorporated herein by reference in their entireties.

We claim:

1. A method for detecting a physiological property of target myocardial tissue, comprising: monitoring the cardiac cycle; non-invasively inducing a tissue displacement at a target myocardial tissue site at a determined time during the cardiac cycle by applying an ultrasound pulse; non-invasively acquiring data relating to an acoustic property of the target myocardial tissue site that is directly related to at least one of myocardial tissue stiffness, myocardial tissue strain or strain rate, myocardial tissue tension and myocardial contractility at or in proximity to the target myocardial tissue site prior to and/or during and/or following the induction of tissue displacement; and relating the acquired data with a physiological property of the myocardial target tissue or a cardiac parameter.

2. A method of claim 1, wherein the data acquired relating to an acoustic property of the target myocardial tissue site is acquired by administering a plurality of acoustic interrogation pulses to the target tissue site and collecting acoustic data from the target tissue site.

3. A method of claim 1, wherein the data relates to at least one of the magnitude, amplitude and phase of acoustic scatter.

4. A method of claim 1, additionally comprising collecting acoustic data from the target myocardial tissue site using an ultrasound transducer operating in at least one of the following modes: transmission mode, reflection mode, scatter mode, backscatter mode, emission mode, echo mode, Doppler mode, color Doppler mode, harmonic or sub-harmonic imaging modes, a-mode, b-mode or in-mode; and correlating the acoustic data relating to the induced tissue displacement with a physiological property of the target tissue.

5. A method of claim 1, wherein the target myocardial tissue site includes or is in proximity to a blood vessel and a physiological property detected is arterial blood pressure.

6. A method of claim 1, additionally comprising comparing the acquired data with an empirically determined standard.

7. A method of claim 1 wherein the target myocardial tissue site comprises myocardial ventricular tissue.

8. A method of claim 1 additionally comprising inducing tissue displacements at the target myocardial tissue site and monitoring at least one of myocardial contractility, myocardial strain and strain rate and/or myocardial tension over a period of at least several cardiac cycles and observing changes in the properties of the target myocardial tissue site over time.

9. A method of claim 1 comprising inducing a tissue displacement and acquiring data relating to an acoustic property of the target myocardial tissue site during diastole.

10. A method of claim 1, additionally comprising applying a plurality of different ultrasound pulses to the target myocardial tissue site and acquiring data relating to acoustic properties induced by the different ultrasound pulses.

11. A method of claim 1, additionally comprising applying a plurality of ultrasound pulses to a plurality of target tissue sites and acquiring data relating to the induced tissue displacements at the plurality of target tissue sites.

12. A method of claim 1, comprising: applying focused ultrasound and inducing oscillation of the target myocardial tissue at the target myocardial tissue site at a determined time during the cardiac cycle; measuring the frequency of an acoustic signal emitted from the target myocardial tissue;

and relating the frequency of the emitted acoustic signal to a physiological tissue property.

13. A method for assessing a physiological property of a target myocardial tissue, comprising the steps of: monitoring the cardiac cycle; acquiring acoustic data relating to intrinsic tissue displacements at a target myocardial tissue site at multiple time points over the course of at least one cardiac cycle, and relating the acoustic data with a physiological property of the target myocardial tissue, wherein said acoustic data is collected by using an ultrasound transducer.

14. The method of claim 13, wherein said ultrasound transducer operates in at least one of the following modes: transmission mode, reflection mode, scatter mode, backscatter mode, emission mode, echo mode, Doppler mode, color Doppler mode, harmonic or sub-harmonic imaging modes, a-mode, b-mode or in-mode; and correlating the acquired acoustic data relating to intrinsic tissue displacement with a physiological property of the target tissue.

15. The method of claim 13, further comprising the step of acquiring acoustic data relating to intrinsic tissue displacements at multiple target tissue sites at multiple time points over the course of at least one cardiac cycle.

16. The method of claim 13, wherein the acoustic data acquired relating to the intrinsic tissue displacement at the target myocardial tissue site relates to acoustic properties of the target myocardial tissue.

17. The method of claim 13, wherein said acoustic properties of the target myocardial tissue are selected from the group consisting of changes in the amplitude of acoustic signals, changes in phase of acoustic signals, changes in frequency of acoustic signals, changes in acoustic emission signals, changes in length of scattered signals relative to an interrogation signal, changes in maximum and/or minimum amplitude of an acoustic signal within a cardiac cycle, the ratio of the maximum and/or minimum amplitude to that of the mean or variance of subsequent oscillations within a cardiac cycle, changes in temporal or spatial variance of scattered signals at different times in the same location and/or at the same time in different locations, and rates of change of tissue displacement or relaxation.

18. The method of claim 13, wherein said acoustic data relating to said intrinsic tissue displacement at the target myocardial tissue site is acquired by administering acoustic interrogation pulses to the target myocardial tissue site and collecting acoustic scatter data.

19. The method of claim 13, further comprising the step of relating the intrinsic tissue displacement data and additional data relating to blood pressure, cardiac and/or respiratory cycles, to a physiological property of said target myocardial tissue.

20. The method of claim 13, wherein said acoustic data is collected using an ultrasound transducer array.

* * * * *